(12) United States Patent
Ortyn et al.

(10) Patent No.: US 7,315,357 B2
(45) Date of Patent: *Jan. 1, 2008

(54) IMAGING AND ANALYZING PARAMETERS OF SMALL MOVING OBJECTS SUCH AS CELLS

(75) Inventors: William E. Ortyn, Bainbridge Island, WA (US); David A. Basiji, Seattle, WA (US)

(73) Assignee: Amnis Corporation, Seattle, WA (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/230,373

(22) Filed: Sep. 20, 2005

(65) Prior Publication Data

US 2006/0066837 A1  Mar. 30, 2006

Related U.S. Application Data

(63) Continuation of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/240,125, filed on Oct. 12, 2000, provisional application No. 60/117,203, filed on Jan. 25, 1999.

(51) Int. Cl.
*G01N 21/00* (2006.01)
*G01N 21/47* (2006.01)
*G01N 21/64* (2006.01)

(52) U.S. Cl. .................. 356/73; 356/318; 356/338
(58) Field of Classification Search .................. 356/73, 356/317, 318, 338
See application file for complete search history.

(56) References Cited

U.S. PATENT DOCUMENTS 3,922,069 A  11/1975  Kishikawa et al. ......... 359/633

(Continued)

FOREIGN PATENT DOCUMENTS

WO  WO 00/42412  7/2000

OTHER PUBLICATIONS

Kubota, Fumio et al. 1995. "Flow Cytometer and Image Device Used in Combination." *Cytometry*: 21:129-132.

(Continued)

*Primary Examiner*—F. L. Evans
(74) *Attorney, Agent, or Firm*—Ronald M. Anderson

(57) ABSTRACT

Light from an object such as a cell moving through an imaging system is collected and dispersed so that it is imaged onto a plurality of separate detectors. The light is spectrally dispersed by a plurality of spaced-apart dichroic reflectors, each detector receiving light from a different one of the dichroic reflectors. Each dichroic filter reflects light of a different predetermined color, passing light of other colors. The output signal from each detector is indicative of a different characteristic of the object. In one configuration, each detector is provided with a separate imaging lens. In another configuration, the detectors are spaced at varying distances from the corresponding dichroic reflectors, so that separate imaging lenses are not required.

53 Claims, 24 Drawing Sheets

U.S. PATENT DOCUMENTS

| | | | |
|---|---|---|---|
| 4,635,293 A | 1/1987 | Watanabe | 382/130 |
| 4,677,680 A | 6/1987 | Harima et al. | 382/112 |
| 4,770,992 A | 9/1988 | Van den Engh et al. | 435/6 |
| 4,786,165 A | 11/1988 | Yamamoto et al. | 356/23 |
| 5,096,807 A | 3/1992 | Leaback | 435/6 |
| 5,141,609 A | 8/1992 | Sweedler et al. | 356/344 |
| 5,153,916 A | 10/1992 | Inagaki et al. | 382/151 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/6 |
| 5,247,339 A | 9/1993 | Ogino | 356/73 |
| 5,247,340 A | 9/1993 | Ogino | 356/73 |
| 5,272,354 A | 12/1993 | Kosaka | 250/574 |
| 5,351,311 A | 9/1994 | Rogers | 382/156 |
| 5,422,712 A | 6/1995 | Ogino | 356/73 |
| 5,444,527 A | 8/1995 | Kosaka | 356/73 |
| 5,471,294 A | 11/1995 | Ogino | 356/73 |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,695,934 A | 12/1997 | Brenner | 435/6 |
| 5,754,291 A | 5/1998 | Kain | 356/344 |
| 5,760,899 A | 6/1998 | Eismann | 356/326 |
| RE35,868 E | 8/1998 | Kosaka | 250/574 |
| 5,831,723 A | 11/1998 | Kubota et al. | 356/73 |
| 5,848,123 A | 12/1998 | Strommer | 378/98.8 |
| 5,855,753 A | 1/1999 | Trau et al. | 204/484 |
| 5,929,986 A | 7/1999 | Slater et al. | 356/326 |
| 5,959,953 A | 9/1999 | Alon | 369/44.41 |
| 6,007,994 A | 12/1999 | Ward et al. | 435/6 |
| 6,014,468 A | 1/2000 | McCarthy et al. | 382/254 |
| 6,066,459 A | 5/2000 | Garini et al. | 435/6 |
| 6,116,739 A | 9/2000 | Ishihara et al. | 353/31 |
| 6,156,465 A | 12/2000 | Cao et al. | 430/30 |
| 6,210,973 B1 | 4/2001 | Pettit | 436/172 |
| 6,211,955 B1 | 4/2001 | Basiji et al. | 356/326 |
| 6,249,341 B1 | 6/2001 | Basiji et al. | 356/73 |
| 6,256,096 B1 | 7/2001 | Johnson | 356/335 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,522,781 B1 | 2/2003 | Norikane et al. | 382/203 |
| 6,549,664 B1 | 4/2003 | Daiber et al. | 382/232 |
| 6,763,149 B2 | 7/2004 | Riley et al. | 382/294 |
| 7,006,710 B2 | 2/2006 | Riley et al. | 382/294 |
| 2001/0006416 A1 | 7/2001 | Johnson | 356/73 |
| 2002/0126275 A1 | 9/2002 | Johnson | 356/317 |

OTHER PUBLICATIONS

Kubota, F. 2003. "Analysis of red cell and platelet morphology using an image-combined flow cytomer." *Clin. Lab. Haem.*: 25:71-76.

Ong, Sim Heng. 1985. Development of a System for Imaging and Classifying Biological Cells in a Flow Cytometer. Doctor of Philosophy Thesis. University of Sydney, School of Electrical Engineering. (August).

Ong, S.H. et al. 1987. "Development of an Image Flow Cytometer." *Analytical and Quantitative Cytology and Histology. XIVth International Conference on Medical and Biological Engineering and the VIIth International Conference on Medical Physics*, Finland. (August):375-382.

Ong, S.H. and P.M. Nickolls. 1991. "Optical Design in a Flow System For Imaging Cells." *Sciences in Medicine*: 14:2:74-80.

Ong, S.H. and P.M. Nickolls. 1994. "Analysis of MTF Degradation in the Imaging of Cells in a Flow System." *International Journal of Imaging Systems & Technology*: 5:243-250.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry*: 48:194-201.

Wang, Fu-sheng and Fumio Kubota. 2002. "A Novel Apoptosis Research Method With Imaging-Combined Flow Cytometer and HITC OR IR-125 Staining." *Cytometry*: 50:267-274.

Wietzorrek, Joachim et al. 1999. "A New Multiparameter Flow Cytometer: Optical and Electrical Cell Analysis in Combination With Video Microscopy in Flow." *Cytometry*: 35:291-301.

10 MICRON CELL 0.5 X 0.5 MICRON PIXEL IMAGE
(NO BINNING)

0.5 X 1.0 MICRON PIXEL IMAGE
(1 X 2 BINNING)

0.5 X 2.0 MICRON PIXEL IMAGE
(1 X 4 BINNING)

0.5 X 4.0 MICRON PIXEL IMAGE
(1 X 8 BINNING)

IMAGING AND ANALYZING PARAMETERS OF SMALL MOVING OBJECTS SUCH AS CELLS

RELATED APPLICATIONS

This application is a continuation application of a patent application Ser. No. 10/628,662, filed on Jul. 28, 2003 now U.S. Pat. No. 6,975,400, which itself is a continuation-in-part application of a patent application Ser. No. 09/976,257, filed on Oct. 12, 2001, now U.S. Pat. No. 6,608,682 issued Aug. 19, 2003, which is a continuation-in-part application of a patent application Ser. No. 09/820,434, filed on Mar. 29, 2001, now U.S. Pat. No. 6,473,176 issued Oct. 29, 2002, which is a continuation-in-part application of patent application Ser. No. 09/538,604, filed on Mar. 29, 2000, now U.S. Pat. No. 6,211,955 issued Apr. 3, 2001, which itself is a continuation-in-part application of patent application Ser. No. 09/490,478, filed on Jan. 24, 2000, now U.S. Pat. No. 6,249,341 issued Jun. 19, 2001, which is based on a provisional application Ser. No. 60/117,203, filed on Jan. 25, 1999, the benefit of the filing dates of which is hereby claimed under 35 U.S.C. § 120 and 35 U.S.C. § 119(e). Copending patent application Ser. No. 09/967,257, noted above, is also based on provisional application Ser. No. 60/240,125, filed on Oct. 12, 2000, the benefit of the filing date of which is hereby claimed under 35 U.S.C. § 119(e).

FIELD OF THE INVENTION

This invention generally relates to imaging moving objects or particles for purposes of analysis and detection, and more specifically, to a system and method for increasing the throughput or analysis rate of an imaging system that utilizes a time delay integration (TDI) detector.

BACKGROUND OF THE INVENTION

There are a number of biological and medical applications that are currently impractical due to limitations in cell and particle analysis technology. Examples of such biological applications include battlefield monitoring of known airborne toxins, as well as the monitoring of cultured cells to detect the presence of both known and unknown toxins. Medical applications include non-invasive prenatal genetic testing and routine cancer screening via the detection and analysis of rare cells (i.e., low rate of occurrence) in peripheral blood. All of these applications require an analysis system with the following principal characteristics:
1. high speed measurement;
2. the ability to process very large or continuous samples;
3. high spectral resolution and bandwidth;
4. good spatial resolution;
5. high sensitivity; and
6. low measurement variation.

Some advances have been made, particularly with the development of spectral based imaging systems that allow for the analysis of large numbers of particles or cells entrained in a flow of fluid.

In particular, a recently developed imaging flow cytometer technology, termed ImageStream™, makes great strides in achieving each of the above noted principle characteristics. These significant advancements in the art of flow cytometry are described in the following commonly assigned patents: U.S. Pat. No. 6,249,341, issued on Jun. 19, 2001 and entitled "Imaging And Analyzing Parameters of Small Moving Objects Such As Cells;" U.S. Pat. No. 6,211,955 issued on Apr. 3, 2001, also entitled "Imaging And Analyzing Parameters of Small Moving Objects Such As Cells;" U.S. Pat. No. 6,473,176, issued on Oct. 29, 2002, also entitled "Imaging And Analyzing Parameters of Small Moving Objects Such As Cells;" U.S. Pat. No. 6,583,865, issued on Jun. 24, 2003, entitled "Alternative Detector Configuration And Mode of Operation of A Time Delay Integration Particle Analyzer;" U.S. patent application Ser. No. 09/989,031 entitled "Imaging And Analyzing Parameters of Small Moving Objects Such As Cells in Broad Flat Flow."

While the current analysis rate is sufficient for many applications, there are a number of applications in which a cell detection event is extremely rare. Specifically, events can occur at the rate of 1 in 1 million to 1 in 10 million, or even greater in the case of non-invasive fetal chromosome assessment and early cancer detection.

It would be desirable to provide improvements to the imaging of particles in flow to enable such technology to be used in conjunction with such rare detection events. It would be desirable to provide methods to increase the throughput or analysis rate of such imaging systems.

SUMMARY OF THE INVENTION

A first aspect of the invention relates to methods and systems for imaging objects entrained in a broad flat flow. In a first embodiment, an imaging system is configured to determine one or more characteristics of an object entrained in a flow of fluid, from an image of the object while there is relative movement between the object and the imaging system. The imaging system includes a fluid channel having a generally elongate cross section, such that the fluid channel directs the flow of fluid into a generally broad flat flow. The system also includes a collection lens disposed so that light from the object entrained in fluid passes through the collection lens and travels along a collection path. A plurality of light reflecting elements are disposed in the collection path. Each light reflecting element reflects light of a different predefined characteristic along a different reflected light path, and passes light that does not have the different predefined characteristic, such that light from the object passes through each light reflecting element only once. The system also includes a plurality of imaging lenses disposed such that for each light reflecting element, at least one imaging lens is positioned to receive one of reflected and transmitted light from that light reflecting element, thereby producing an image. Each such image is projected toward a different predetermined location. At least one of the plurality of imaging lenses has a focal length differing from another of the plurality of imaging lenses, such that at least one of the plurality of imaging lenses generates a first image having a magnification that is different than a second image generated by another of the plurality of imaging lenses. Finally, the system includes a plurality of detectors disposed such that for each imaging lens, a detector is positioned to receive an image projected by a different imaging lens. Each detector produces an output signal that is indicative of a different characteristic of the object while the relative movement between the object and the imaging system occurs.

Preferably, each of the plurality of detectors is a TDI detector. Each TDI detector produces an output signal by integrating light from at least a portion of the object over time, while the relative movement between the object and the imaging system occurs.

Another aspect of the present invention is directed to a method for determining one or more characteristics of a moving object from a plurality of images of the object, while there is relative movement between the object and the imaging system, based upon light from the object. The method includes the step of introducing the object into a fluid channel having a generally elongate cross section, such that the fluid channel directs the flow of fluid into a generally broad flat flow. While the object is disposed within the generally broad flat flow, light from the object is focused along a collection path in a direction that is different than the direction of the relative movement between the object and the imaging system. Then the object is imaged using the focused light. At each of a plurality of successive points disposed along the collection path, light of a predefined characteristic is reflected, while light that does not have the predefined characteristic is allowed to pass. Each different point at which such reflection or passing occurs is associated with a different predefined characteristic. A plurality of TDI detectors are employed to receive either light that was reflected or light that was transmitted at each successive point. Each TDI detector produces an output signal, which is analyzed to determine at least one characteristic of the object.

Yet aspect of the present invention is directed to a light dispersing component positioned along an optical axis. The light dispersing component includes a plurality of light reflecting elements, each of which reflects light of a predefined characteristic and passes light that does not have that characteristic. Each light reflecting element is positioned at a different angle with respect to the optic axis to direct light of the predefined characteristic in a direction or at an angle different from that of other light reflecting elements. The different angles range from about 44 degrees to about 46 degrees relative to the optic axis. Each light reflecting element is positioned adjacent to a preceding light reflecting element such that light reflected by all but a first light reflecting element in the light dispersing component passes through at least one preceding light reflecting element a second time.

Preferably, wedge-shaped substrates define an angular difference between each light reflecting element, and light reflecting surfaces of the light reflecting elements are sandwiched between the wedge-shaped substrates, forming a monolithic structure. Also preferably, the light reflecting elements reflect light based on a spectral content of the light. The light reflecting elements can be configured to reflect light as a function of a polarization characteristic of that light.

Still another aspect of the present invention is directed to a method for increasing the throughput or analysis rate of an imaging system that use a TDI detector. Binning can be used to achieve such an increase.

One embodiment employs a multi-tap TDI CCD camera to enable an increase in line rate readout rates. For example, if the instrument uses a 600 by 512 pixelated CCD detector, and the 600 row element detector includes six separate multispectral imaging channels that are read out utilizing one tap so that six separate taps are used to read off the six separate imaging channels, the speed of the camera can be increased by a factor of six.

Another embodiment uses broad flat flow to increase the rate of analysis. A rectangular cross sectional fluid channel is employed, instead of a square cross sectional core, to enable a broad flat flow to be achieved. A broad flat flow enables multiple objects to be imaged, which further increases the analysis rate.

Yet another embodiment of the invention uses binning of the vertical CCD elements, such that the number of rows decrease, thereby increasing the effective read out rate for the output signal of the TDI detector. The decrease in vertical image resolution provides a substantial increase in analysis rate. It is important to note that the binning is only in the vertical direction, and that there is no binning in the horizontal direction.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 28:
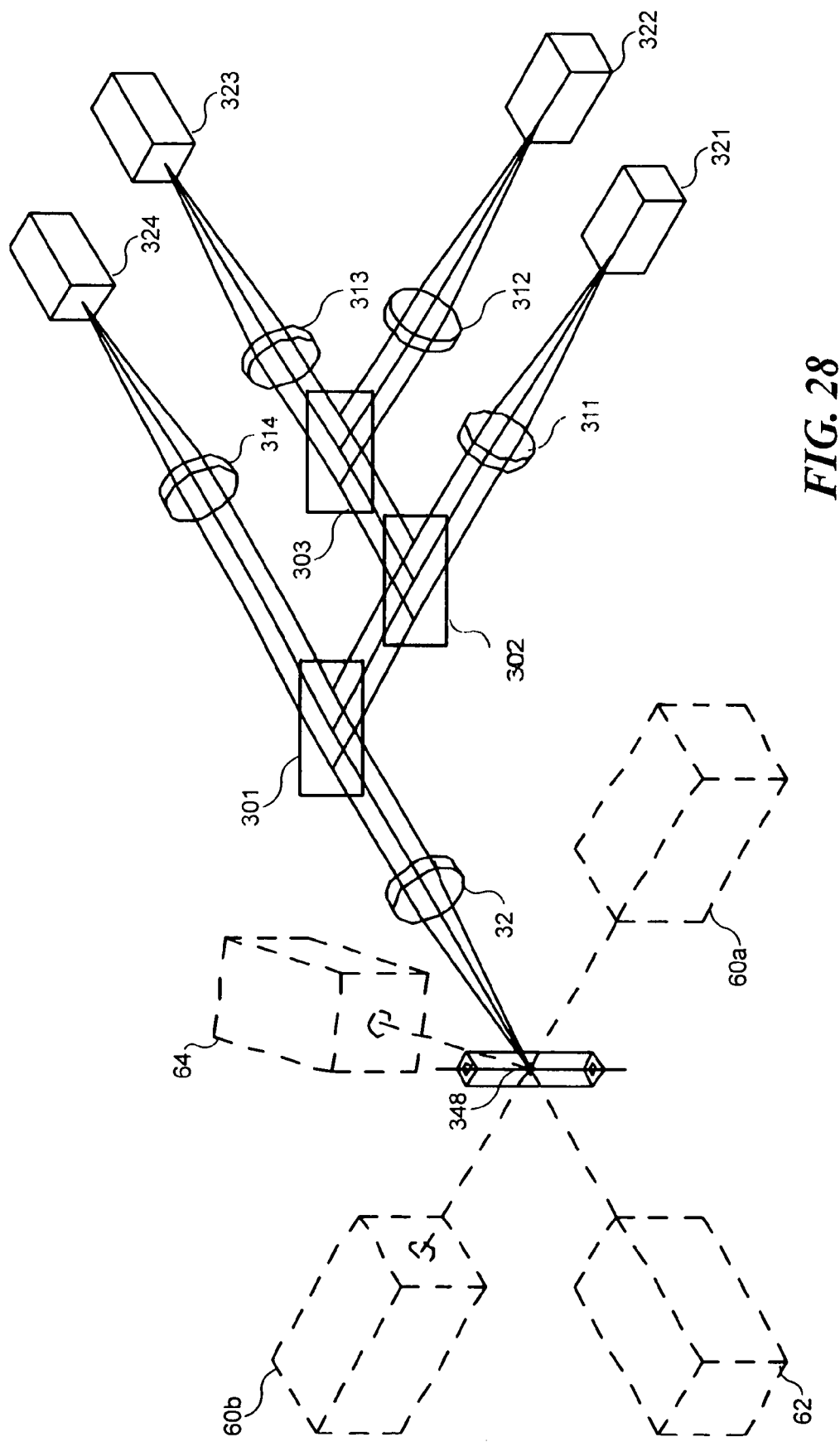
FIG. 28 is an isometric view of an alternate embodiment employing separate TDI detectors receiving both light transmitted through and reflected by spectral decomposition elements.
Figure 29A:
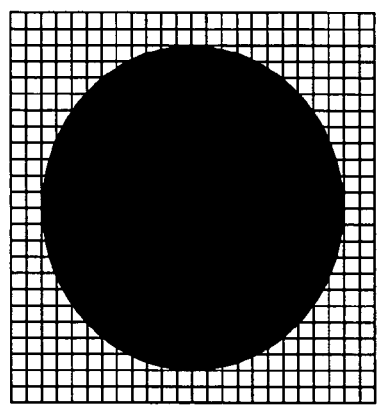
Figure 29B:
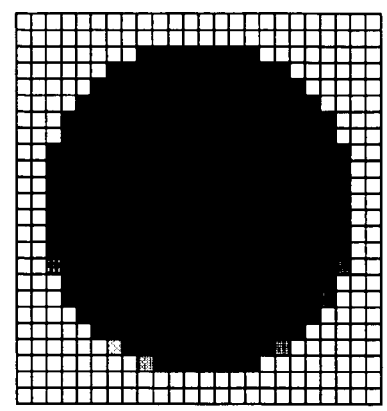
Figure 29C:
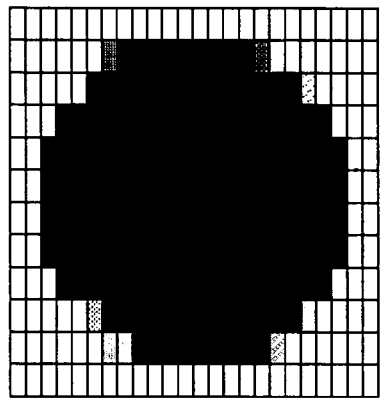
Figure 29D:
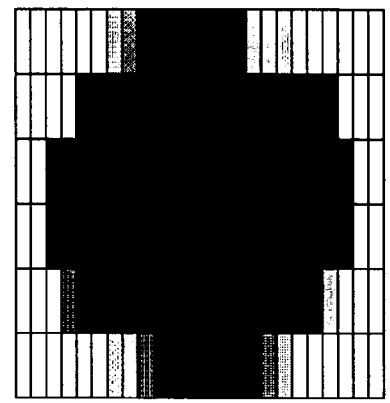
Figure 29E:
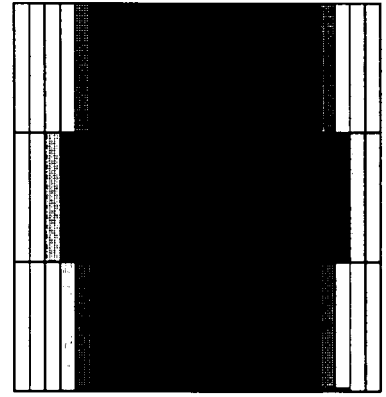

FIG. 29A schematically illustrates a 10 micron particle;

FIG. 29B schematically illustrates a 0.5×0.5 micron pixel image of the micron particle of FIG. 29A obtained with an imaging system using a pixelated TDI detector;

FIG. 29C schematically illustrates a 0.5×1.0 micron pixel image of the micron particle of FIG. 29A, obtained after processing the image of FIG. 28B using 1×2 binning;

FIG. 29D schematically illustrates a 0.5×2.0 micron pixel image of the micron particle of FIG. 29A, obtained after processing the image of FIG. 28B using 1×4 binning; and FIG. 29E schematically illustrates a 0.5×4.0 micron pixel image of the micron particle of FIG. 29A, obtained after processing the image of FIG. 28B using 1×8 binning.

DESCRIPTION OF THE PREFERRED EMBODIMENTS

Overview

A first aspect of the present invention relates to a system and method for imaging particles entrained in a broad flat flow. To achieve this type of flow, a fluid channel having a generally elongate cross section is employed to direct the flow of fluid into a generally broad, flat configuration. Such fluid channels can be integrated into many different embodiments of imaging systems, several of which are described below.

A second aspect of the present invention relates to a binning method for a pixilated detector that enables an increase in the detection/analysis rate of cells or objects that are in motion relative to the detector. This binning technique has been developed to increase the analysis rate of a recently developed imaging flow cytometer technology, embodied in an ImageStream™ product. These significant advancements in the art of flow cytometery are described in the following commonly assigned patents that were noted above, in the Background of the Invention. Technical descriptions of multiple embodiments of imaging systems in accord with these patents are provided below. The advantages of binning techniques in accord with the present invention are described below in the section entitled "Methods to Enhance the Analysis Rate for Imaging Systems including TDI Detectors."

Preferred Embodiments of Imaging Systems

The imaging systems described below have considerable advantages over more conventional systems employed for cell and particle analysis. These advantages arise from the use in several of the imaging systems of an optical dispersion system, in combination with a TDI detector that produces an output signal in response to the images of cells and other objects that are directed on the TDI detector. Multiple objects can be imaged on the TDI detector at the same time. In addition, the image of each object can be spectrally decomposed to discriminate object features by absorption, scatter, reflection or probe emissions using a common TDI detector for analysis.

These imaging systems can be employed to determine morphological, photometric, and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can either be stimulated into fluorescence or phosphorescence to emit light, or may be luminescent, producing light without stimulation. In each case, the light from the object is imaged on the TDI detector of the present invention to determine the presence and amplitude of the emitted light, the number of discrete positions in a cell or other object from which the light signal(s) originate(s), the relative placement of the signal sources, and the color (wavelength or waveband) of the light emitted at each position in the object.

An initial application of the imaging system comprising the present invention will likely be employed as a cell analyzer to determine one or more of the parameters listed above, for cells entrained in a fluid flowing through the imaging system. However, it should also be understood that this invention can be used for imaging other moving objects.

First Preferred Embodiment of Imaging System

Figure 1:
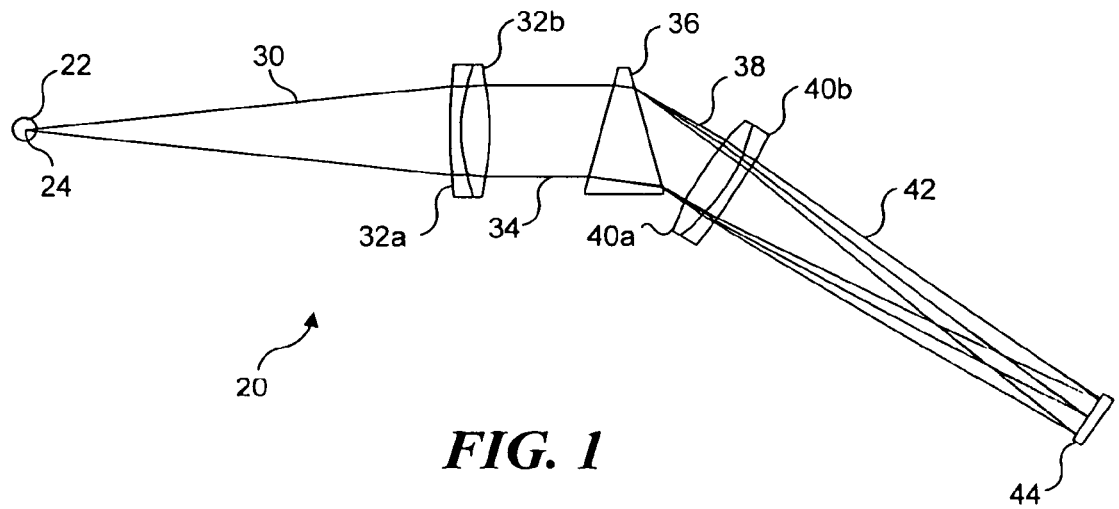
FIG. 1 is a plan view of a first embodiment of the present invention in which particles conveyed by a fluid stream are depicted as flowing into the sheet.
Figure 2:
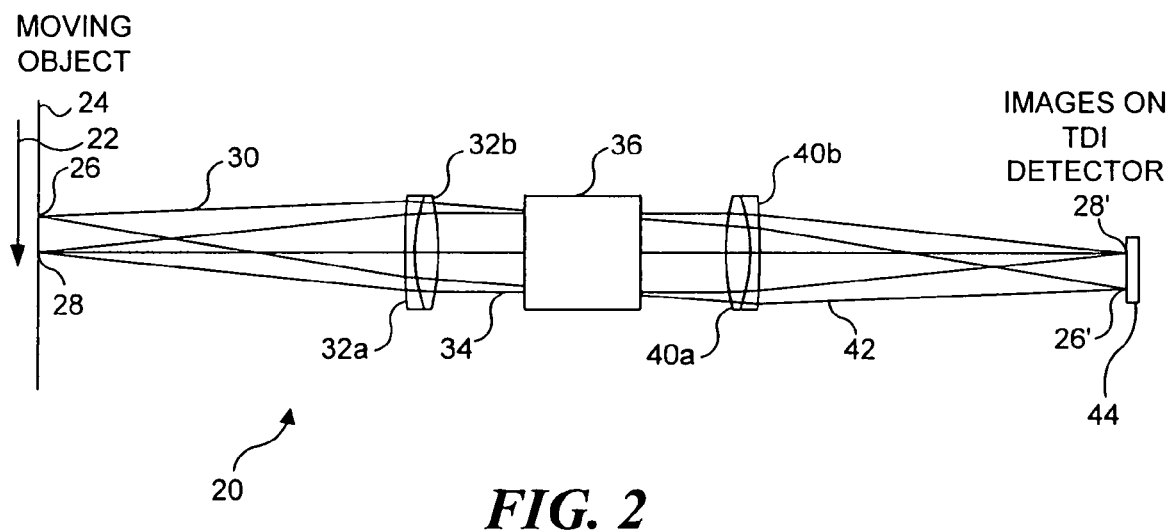
FIG. 2 is a side elevational view of the first embodiment shown in FIG. 1.
Figure 3:
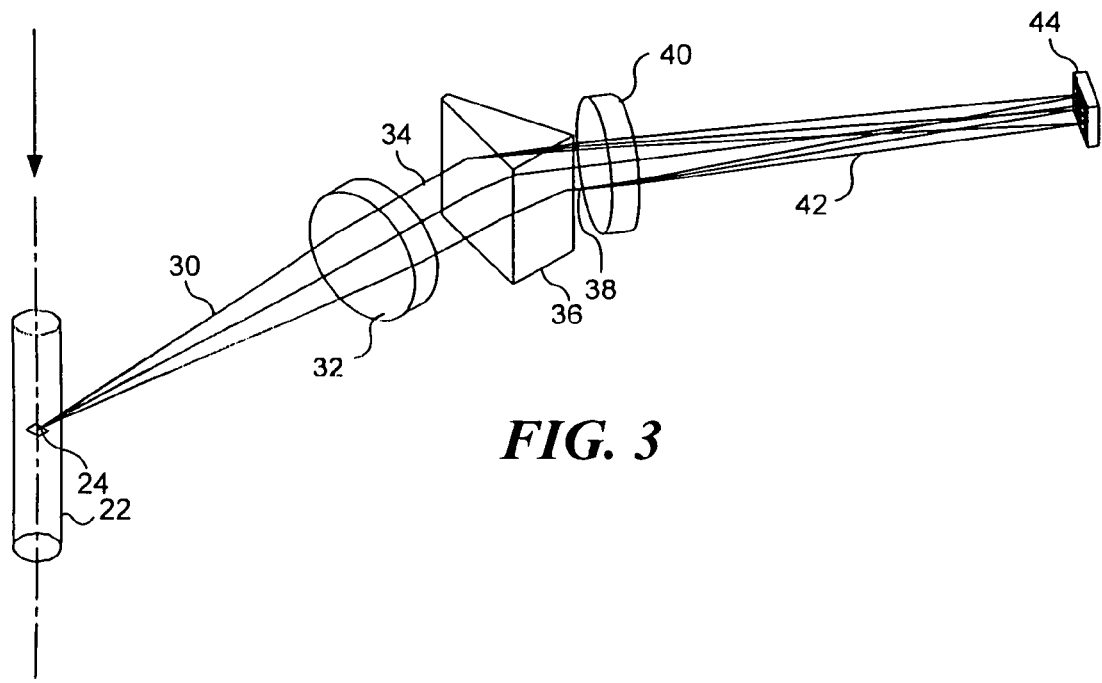
FIG. 3 is an isometric view of the first embodiment of FIG. 1.

A first preferred embodiment of an imaging system 20 that is useful in applying the present invention is schematically illustrated in FIGS. 1, 2, and 3, in connection with producing images of moving objects such as cells that are conveyed by a fluid flow 22 through the imaging system. In FIG. 1, fluid flow 22 entrains an object 24 (such as a cell, but alternatively, any type of small particle) and carries the object through the imaging system. The direction of the fluid flow in FIG. 1 is into (or out of) the sheet, while in FIGS. 2 and 3, the direction of flow is from top to bottom, as indicated by the arrow to the left of the Figures. Light 30 from object 24 passes through collection lenses 32*a* and 32*b* that collect the light, producing collected light 34, which is approximately focused at infinity, i.e., the rays of collected light from collection lens 32*b* are generally parallel. Collected light 34 enters a prism 36, which disperses the light, producing dispersed light 38. The dispersed light then enters imaging lenses 40*a* and 40*b*, which focus light 42 onto a TDI detector 44.

As will be evident in FIG. 2, if the Figure is viewed as depicting the imaging of object 24 over time, the object is shown at both a position 26 and a position 28 as it moves with fluid flow 22. As a consequence, images of object 24 are produced on the detector at two discrete spatial positions 26' and 28', as indicated on the right side of FIG. 2. Alternatively, when FIG. 2 is viewed as depicting a single instant in time, positions 26 and 28 represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32*a* and 32*b*. Lens elements of different designs, either simpler or more complex, could be used in constructing the imaging system to provide the desired optical performance, as will be understood by those of ordinary skill in the art. The actual lenses or optical elements used in the imaging system will depend upon the particular type of imaging application for which the imaging system will be employed.

In each of the preferred embodiments of the present invention, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion but either in different directions or at different rates.

The TDI detector that is used in the various embodiments of the present invention preferably comprises a rectangular charge-coupled device (CCD) that employs a specialized pixel read out algorithm, as explained below. Non-TDI CCD arrays are commonly used for 2-dimensional imaging in cameras. In a standard CCD array, photons that are incident on a pixel produce charges that are trapped in the pixel. The photon charges from each pixel are read out of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other embodiments of the present invention that employ a fluid flow to carry objects through the imaging system, a flow-through cuvette or a jet (not shown) contains the cells or other objects being analyzed. The velocity and cellular concentration of the fluid may be controlled using syringe pumps, gas pressure, or other pumping methods/devices (not shown) to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed, also depending of course, on the actual size of the object being imaged and its distance from the imaging system. It is envisioned that the present invention can have applications ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multi-channel plate imaging devices might also be used for the TDI detector in the present invention. It is important to understand that any pixelated device (i.e., a device having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired affect.

Second Preferred Embodiment

Figure 4:
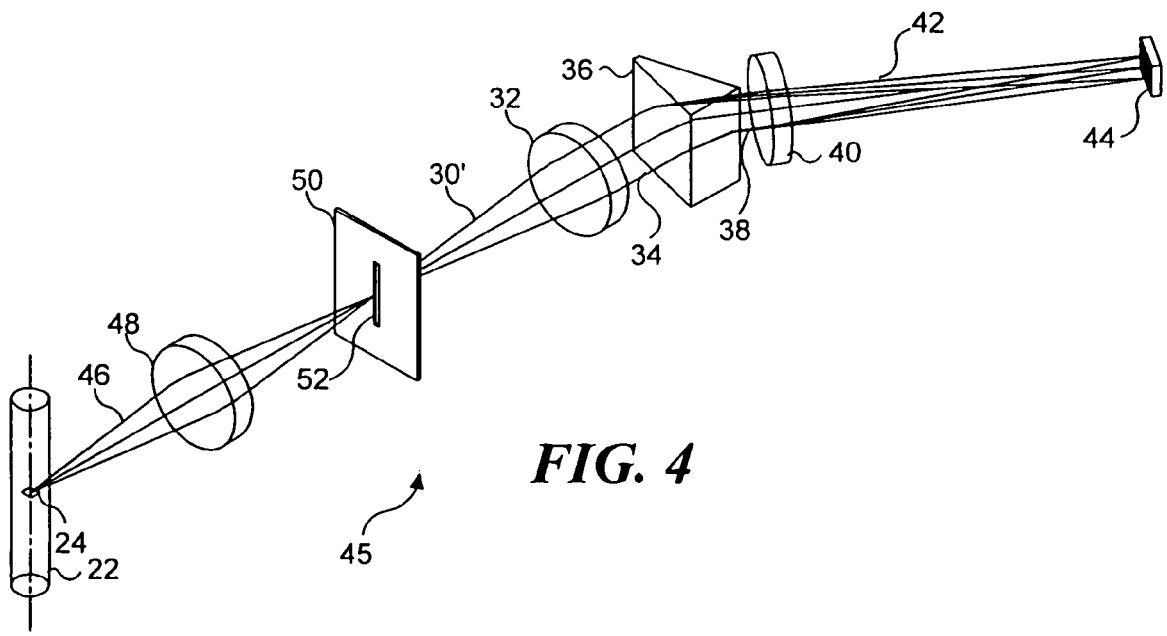
FIG. 4 is an isometric view of a confocal embodiment that includes a slit used for spatial filtering of extraneous light.

FIG. 4 illustrates an imaging system 45, which is a second preferred embodiment in connection with the present invention and which is similar in many ways to imaging system 20. However, imaging system 45 is a confocal embodiment that includes a slit 52 that substantially prevents extraneous light from reaching TDI detector 44. In imaging system 45, light 46 from object 24 is focused by an objective lens 48 onto a slit 52. Slit 52, as shown in FIG. 4, is sufficiently narrow to block light, which is not focused onto the slit by objective lens 48 from passing through the slit. Light 30' passes through the slit and is collected by collection lens 32 as discussed above, in regard to imaging system 20. Collected light 34 is spectrally dispersed by prism 36, and is imaged by imaging lens 40 onto TDI detector 44, also as discussed above. By excluding light other than that from object 24 from reaching TDI detector 44, the TDI detector produces an output signal that corresponds only to the actual images of the object, and the signal is not affected by the extraneous light, which has been excluded. If not excluded in this manner, the ambient light reaching TDI detector 44 might otherwise produce "noise" in the output signal from the TDI detector.

It should be noted that in the illustration of each of imaging systems 20 and 45, a light source has not been shown. These first two embodiments have been illustrated in their most general form to make clear that a separate light source is not required to produce an image of the object, if the object is luminescent, i.e., if the object produces light. However, many of the applications of the present invention will require that one or more light sources be used to provide light that is incident on the object being imaged. The location of the light sources substantially affects the interaction of the incident light with the object and the kind of information that can be obtained from the images on the TDI detector.

Figure 5:
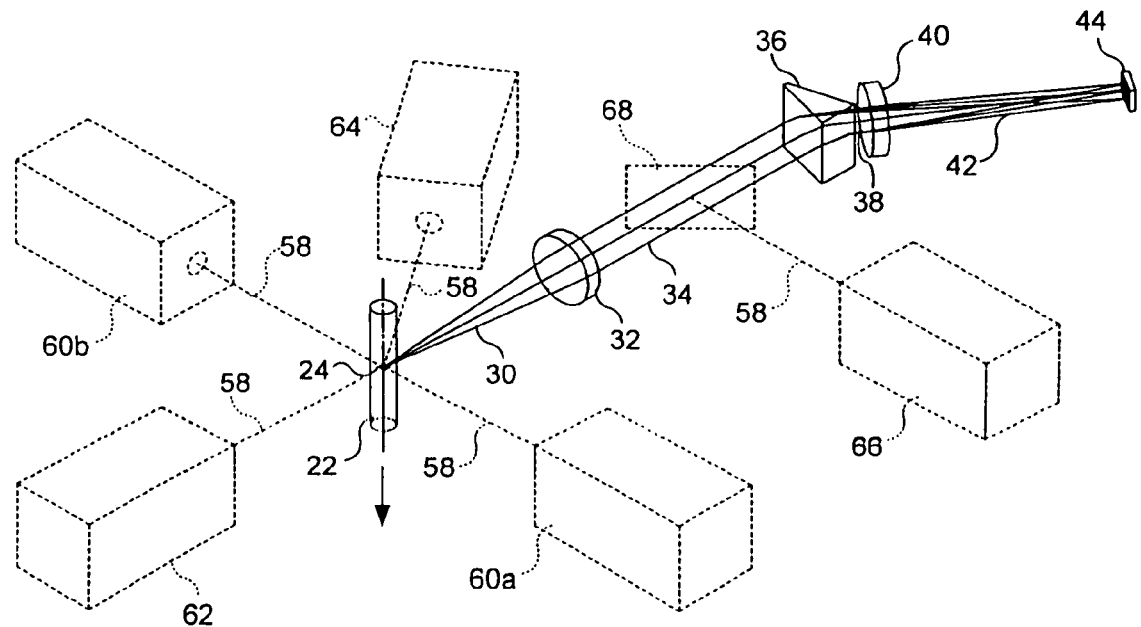
FIG. 5 is an isometric view showing different locations for a light source, in connection with the first embodiment.

In FIG. 5, several different locations of light sources usable to provide light incident on object 24 are illustrated. It should be understood, however, that light sources can be located at many other positions besides those shown in FIG. 5. The location of each light source employed will depend upon the kind of imaging of the object desired, and the data for the object to be derived from the signal produced by the TDI detector. For example, employing a light source 60a or a light source 60b, as shown in the Figure, will provide light 58 that is incident on object 24 and which is scattered from the object into the optical axis of collection lens 32. The optical axis of collection lens 32 is at about a 90° angle relative to the directions of the light incident upon object 24 from either light source 60a or 60b.

In contrast, a light source 62 is disposed so that light 58 emitted from the source travels toward the object in a direction that is generally aligned with the optical axis of collection lens 32, so that the image formed on TDI detector 44 will not include light absorbed by object 24. Light absorption characteristics of the object can thus be determined by illuminating the object using a light source 62.

A light source 64 is disposed to illuminate object 24 with light 58 directed toward the object along a path that is approximately 30-45° off the optical axis of collection lens 32. Light 58, when incident on object 24, will be reflected (scattered) from the object 24, and the reflected or scattered light will be imaged on TDI detector 44. A more directly reflected light is provided by an epi light source 66, disposed so as to direct its light 58 toward a partially reflective surface 68 that is disposed so that a portion of the light is reflected through collection lens 32 and onto object 24. The light reaching the object will be reflected from it back along the axis of collection lens 32 and will at least in part pass through partially reflective surface 68 to form an image of the object on TDI detector 44. Alternatively, a dichroic mirror may be employed instead of, and in the position of, partially reflective surface 68 to direct light from epi light source 66 to excite fluorescence or other stimulated emission from object 24. Emission from object 24 is then at least partially collected by collection lens 32 and passes through the dichroic mirror for spectral dispersion and detection by the TDI detector.

In addition to imaging an object with the light that is incident on it, a light source can also be used to stimulate emission of light from the object. For example, FISH probes that have been inserted into cells will fluoresce when excited by light, producing a corresponding characteristic emission spectra from any excited FISH probe that can be imaged on TDI detector 44. In FIG. 5, light sources 60a, 60b, 64, or 66 could alternatively be used for causing the excitation of FISH probes on object 24, enabling TDI detector 44 to image FISH spots produced by the FISH probes on the TDI detector at different locations as a result of the spectral dispersion of the light from the object that is provided by prism 36. The disposition of these FISH spots on the TDI detector surface will depend upon their emission spectra and their location in the object. Use of FISH probes in connection with producing images of FISH spots on the TDI detector with the present invention is discussed in greater detail below.

Each of the light sources illustrated in FIG. 5 produces light 58, which can either be coherent, non-coherent, broadband or narrowband light, depending upon the application of the imaging system desired. Thus, a tungsten filament light source can be used for applications in which a narrowband light source is not required. For applications such as stimulating the emission of fluorescence from FISH probes, narrowband laser light is preferred, since it also enables a spectrally-decomposed, non-distorted image of the object to be produced from light scattered by the object. This scattered light image will be separately resolved from the FISH spots produced on TDI detector 44, so long as the emission spectra of any FISH spots are at different wavelengths than the wavelength of the laser light. The light source can be either of the continuous wave (CW) or pulsed type. If a pulsed type illumination source is employed, the extended integration period associated with TDI detection can allow the integration of signal from multiple pulses. Furthermore, it is not necessary for the light to be pulsed in synchronization with the TDI detector.

Pulsed lasers offer several advantages over CW lasers when used as a light source in the present invention, including smaller size, higher efficiency, higher reliability, and the ability to deliver numerous wavelengths simultaneously. Another advantage of pulsed lasers is their ability to achieve saturating levels of fluorescence excitation of fluorescent probes used in cells. Fluorescence saturation occurs when the number of photons encountering a fluorescent molecule exceeds its absorption capacity. Saturating excitation produced by a pulsed laser is inherently less noisy than unsaturating CW laser excitation because variations in pulse-to-pulse excitation intensity have little effect on the fluorescence emission intensity.

Prism 36 in the imaging systems discussed above can be replaced with a diffraction grating, since either a prism or a diffraction grating is capable of spectrally dispersing the optical signals from the cells over the pixels of the TDI detector. In addition to providing useful data from a cell or other object, spectral dispersion can be used to reduce measurement noise. In cases where the light source wavelength differs from the emission spectra of the fluorescent probes, the light from the source that is scattered into the collection system is spatially isolated from the fluorescence signals. If the light source wavelength overlaps the emission spectra of the fluorescent probes, the pixels of the TDI detector in which light of the wavelength of the source falls can be isolated from those pixels on which the remaining fluorescence signals fall. Furthermore, by dispersing the fluorescence signals over multiple pixels, the overall dynamic range of the imaging system is increased.

Third Preferred Embodiment

Figure 6:
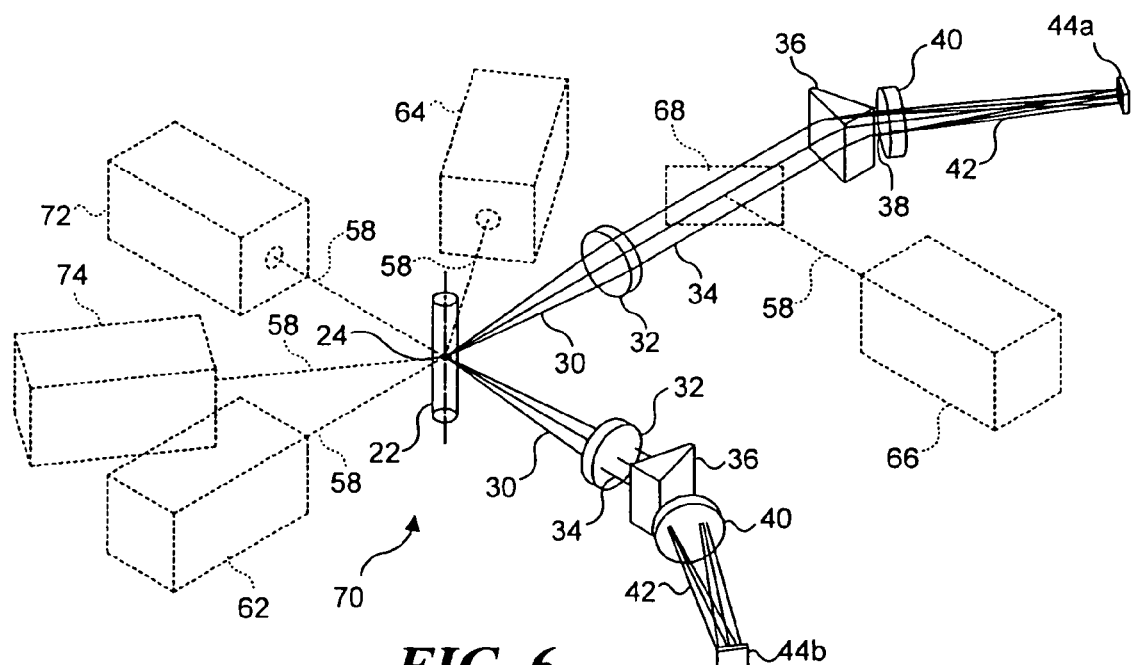
FIG. 6 is an isometric view of another embodiment in which a second set of imaging components and TDI detector are included for monitoring light from a particle, to avoid interference between FISH probes, and showing alternative locations for light sources.

A third preferred embodiment of an imaging system in connection with the present invention is a stereoscopic arrangement 70 of the first preferred embodiment, as illustrated in FIG. 6. This arrangement enables the imaging of the object from two different directions in order to distinguish features that would otherwise overlap when viewed from a single direction. While the third preferred embodiment can be employed for objects on moving substrates such as microscope slides, it is particularly useful for analyzing multi-component objects in solution, such as cells containing FISH probes. Such probes appear as point sources of light anywhere within the cell's three-dimensional nucleus. In some cases, two or more FISH probes may appear in an overlapping relationship along the optical axis of the imaging system. In such cases, one of the FISH probes may obscure the others, making it difficult to determine the number of probes present in the cell. This consideration is a key factor in the determination of genetic abnormalities such as trisomy 21, otherwise known as Down syndrome. Single-perspective systems may address this problem by "panning through" the object along the optical axis to acquire multiple image planes in the object. While this method may be effective, it requires a significant amount of time to collect multiple images and cannot be readily applied to a cell in flow. The stereoscopic imaging system 70 in FIG. 6 includes two TDI detectors 44a and 44b, and their associated optical components, as discussed above in connection with imaging system 20.

By positioning the optical axes of collection lenses 32 for the two TDI detectors so that they are spaced apart, for example, by 90°, it is possible to separately resolve the FISH spots imaged from two or more FISH probes on at least one of TDI detectors 44a or 44b. If two or more FISH probes overlap in regard to the image produced on one of the TDI detectors, they will be separately resolved in the spectrally dispersed images produced on the other TDI detector. Further, the use of two TDI detectors in imaging system 70 in what might be referred to as a "stereo or three-dimensional configuration" provides flexibility in the configuration of each leg of the system, including choice of parameters such as the relative TDI readout rates, axial orientations, inclinations, focal plane positions and magnification. Multiple cells or other objects may be imaged onto each detector simultaneously in the vertical direction. Since the objects may move in synchronicity with the signal on the TDI, no gate or shutter is required to prevent blurring of the image. As previously noted, the present invention can use a pulsed or CW light source without need for a trigger mechanism to time a pulse coincident with particle arrival in the field of view. If a pulsed light source is used, the extended field of view in the axis of motion associated with TDI detection allows the cell or object in motion to be illuminated by multiple pulses during its traversal. In contrast to a frame-based imaging apparatus, a TDI system can produce a single unblurred image of the object that integrates the signal from multiple pulses. When a CW light source is used, the signal generated by the object will be collected throughout the entire traversal of the object through the field of view, as opposed to only a small segment in time when a shutter is open. Therefore, the amount of signal collected and imaged on the detector in the present invention is substantially greater than that of the prior art frame-based imaging systems. Consequently, the present invention can operate at very high throughput rates with excellent signal-to-noise ratio.

Also illustrated in FIG. 6 are several exemplary positions for light sources, which are useful for different purposes in connection with the imaging system illustrated therein. In connection with TDI detector 44a, light source 62 provides illumination of object 24 from a direction so that absorption characteristics of the object can be determined from the image produced on the TDI detector. At the same time, light provided by light source 62 that is scattered from object 24 can be used to produce a scatter image and spectrally dispersed images on TDI detector 44b. Light source 74 can be employed to produce spectrally dispersed and scattered images on both TDI detectors 44a and 44b. If light sources 62 and 72 are of different wavelengths and an appropriate filter is provided to block the wavelength from the light source aligned with the optical axis of the respective collections lenses 32, these two light sources can be used for producing scattered light from the object. For example, suppose light source 72 produces light of a wavelength A that scatters from object 24 and is directed toward TDI detector 44a. By including a filter (not shown) that blocks wavelength B produced by light source 62, the light at wavelength B will not directly affect the images produced on TDI detector 44a. Similarly, the light from light source 72 would be blocked with an appropriate filter (not shown) so that it does not interfere with the imaging of light produced by light source 62 that is scattered from object 24 onto TDI detector 44b.

Epi light source 66 is also illustrated for use in producing images on TDI detector 44a in conjunction with partial reflector 68. Light source 64 can be used to generate reflected light to produce images on TDI detector 44a, while scattered light from this source is directed toward TDI detector 44b. As shown in FIGS. 5 and 6, several different illumination systems may be employed to illuminate objects in flow. A standard approach involves illuminating the objects in flow with a laser path oriented orthogonal to the imaging system. Alternative modes of illumination, such as those shown and FIGS. 5 and 6 and discussed above, allow for the generation of bright field, dark field, phase contrast, fluorescence and EPI fluorescence imagery. These and other possible locations of light sources will be apparent to those of ordinary skill in the art, as appropriate for providing the incident light on the object needed to achieve imaging, depending upon the particular application and information about the object that is desired.

Imaging Slide or Object Carried by Slide

Figure 7:
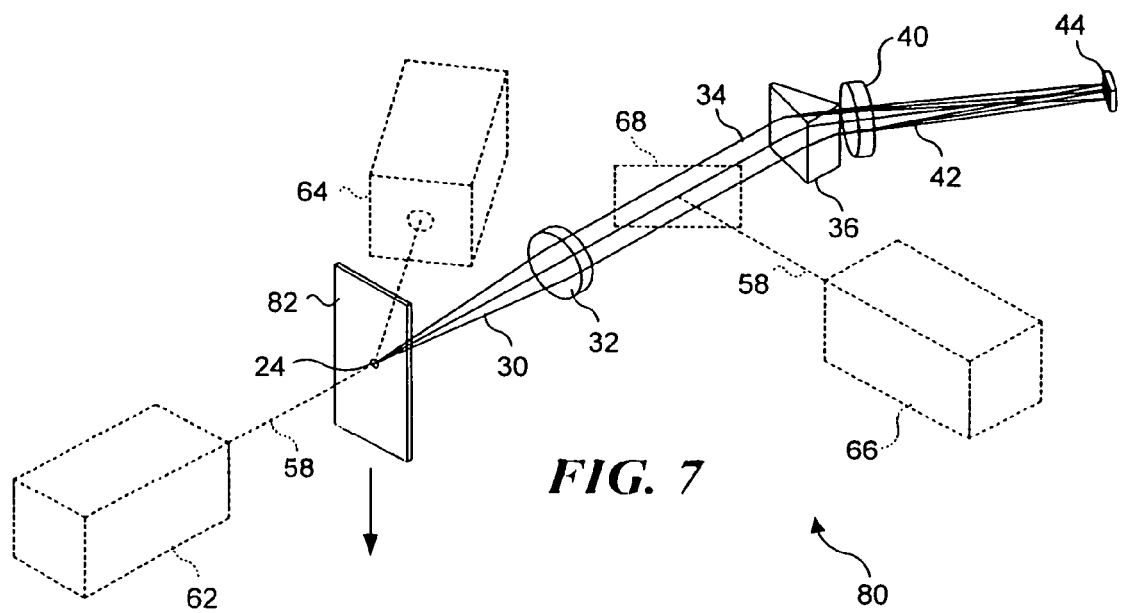
FIG. 7 is an isometric view of an embodiment in which an object is supported by a slide that moves past a collection lens, showing different locations for a light source.

Turning now to FIG. 7, an imaging system 80 is illustrated that is similar to imaging system 20, except that it is used for imaging object 24 on a slide 82. Object 24 is supported by slide 82, and the slide moves relative to the imaging system, as shown in FIG. 7. Alternatively, slide 82 may be the object that is imaged. In this case, the object may be a semiconductor wafer, paper, or other object of interest, since the object may be imaged using reflected incident light.

To provide light incident on either slide 82 or object 24 that is supported thereby, a light source placed at one of several different locations can be employed. Exemplary light sources 62, 64, and 66 illustrate some of the locations at which light sources useful in this embodiment may be disposed. Light 58 emitted by any of the light sources can be either coherent or non-coherent light, pulsed or CW, and can be directed through slide 82 (if it is transparent) from light source 62 or can be reflected from the object or slide, if light sources 64 or 66 are employed. As noted previously, epi light source 66 illuminates the object in connection with a partially reflective surface 68.

Fourth Preferred Embodiment

Figure 8A:
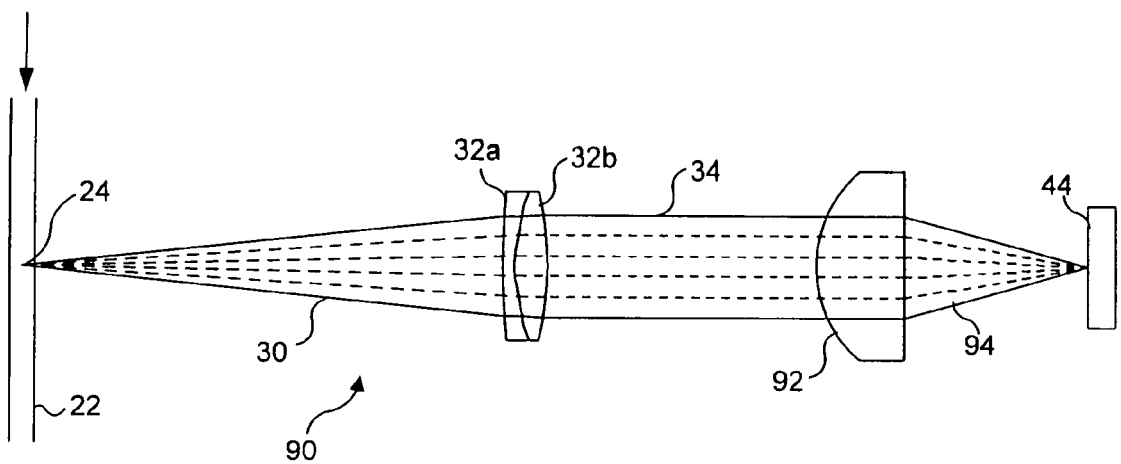
FIGS. 8A and 8B are respectively a plan view and a side elevational view of an alternative to the embodiment of FIG. 7, which is used to produce a scattered pattern on the TDI detector.
Figure 8B:
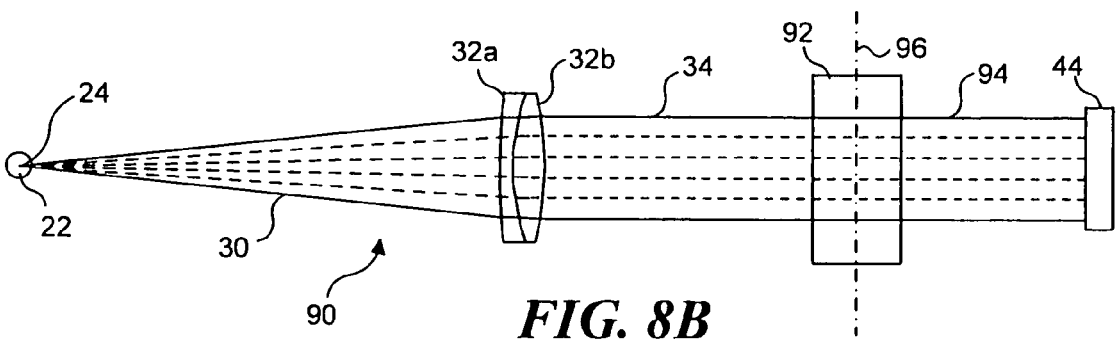

FIGS. 8A and 8B show two different views of a fourth preferred embodiment, which is an imaging system 90 that produces a scattered pattern image of object 24 on TDI detector 44. Light 30 from object 24 passes through collection lenses 32a and 32b, and collected light 34 is directed onto a cylindrical lens 92, as in the previous embodiments. Cylindrical lens 92 focuses light 94 on TDI detector 44, generally along a line that is aligned with a central axis 96 of cylindrical lens 92. Central axis 96 is shown in FIG. 8B, and it will be apparent that it is orthogonal to the direction in which object 24 moves through or relative to the imaging system. As object 24 moves downwardly, relative to its disposition as shown in FIG. 8A, the focus of cylindrical lens 92 on TDI detector 44 moves upwardly. Cylindrical lens 92 thus distributes an image of the object along a row or rows of the light sensitive regions or pixels of TDI detector 44.

Fifth Preferred Embodiment

Figure 9:
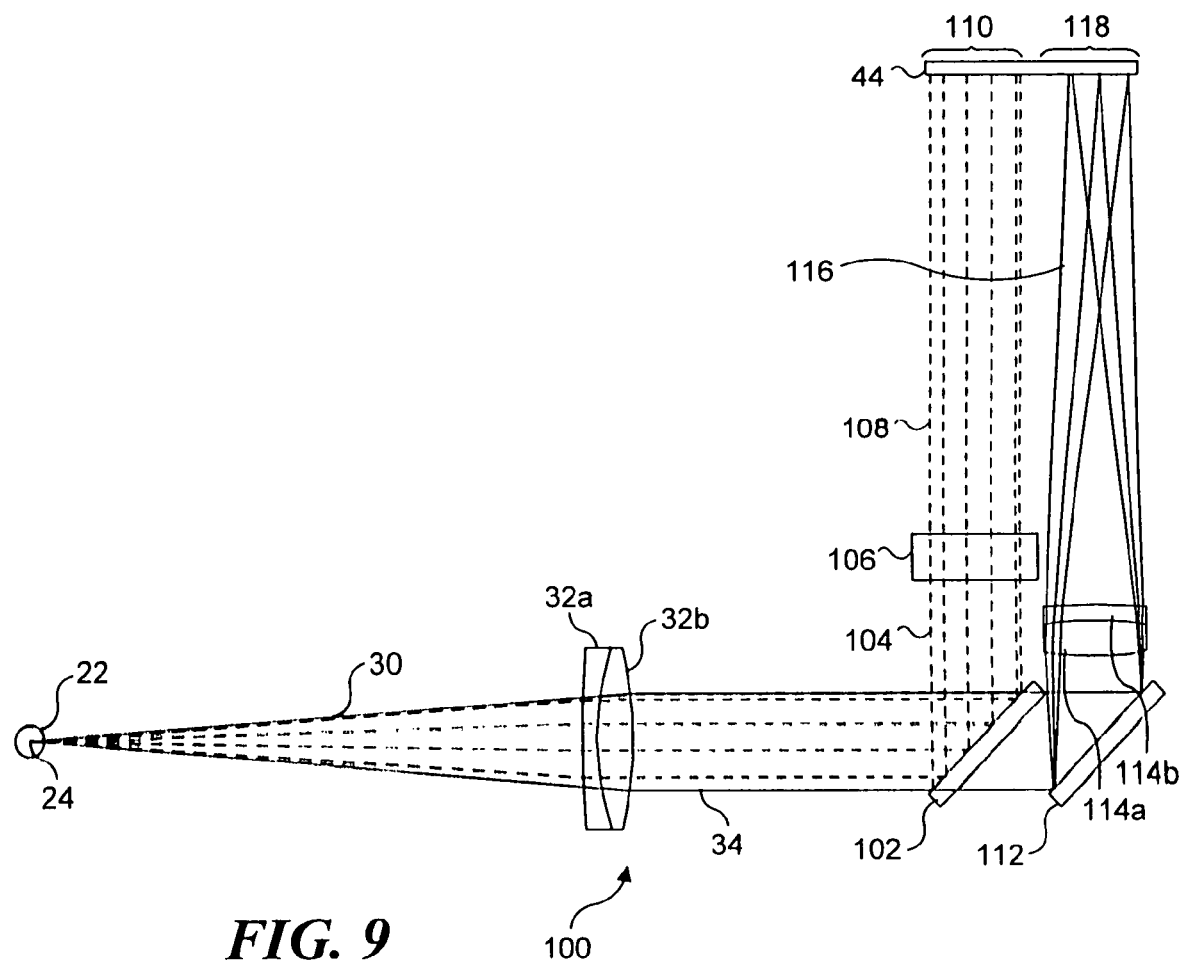
FIG. 9 is a plan view of yet a further embodiment in which light forming a scatter patterned image and spectrally dispersed light from the object are imaged on separate portions of a TDI detector.

Referring now to FIG. 9, an illustration of a fifth preferred embodiment is provided of an imaging system 100 that produces both a scattered pattern image and a spectrally dispersed image of object 24 on TDI detector 44. In imaging system 100, light 30 from object 24 passes through collections lenses 32a and 32b, which produce infinitely focused light 34 directed toward a dichroic filter 102. Dichroic filter 102 reflects light of a specific wavelength, e.g., the wavelength of a light source (not shown) that is incident upon object 24. Light of any other wavelength is transmitted through dichroic filter 102 toward a diffraction grating 112. Diffraction grating 112 spectrally disperses the light transmitted through dichroic filter 102, which typically would be light produced by the fluorescence of FISH probes on object 24, so that a plurality of FISH spots corresponding to the number of different FISH probes and objects being imaged are produced on TDI detector 44.

Light 104, which is reflected from dichroic filter 102 is transmitted into cylindrical lens 106 and is focused along a line as a scattered pattern image in a region 110 on the TDI detector. The spectrally dispersed images of FISH spots or other aspects of object 24 having wavelengths different than that reflected by dichroic filter 102 are imaged as light 116 by imaging lenses 114a and 114b onto a region 118 of the TDI detector. Thus, both signals corresponding to the scattered pattern image and to the spectrally dispersed images are produced by TDI detector 44.

Sixth Preferred Embodiment

Figure 10:
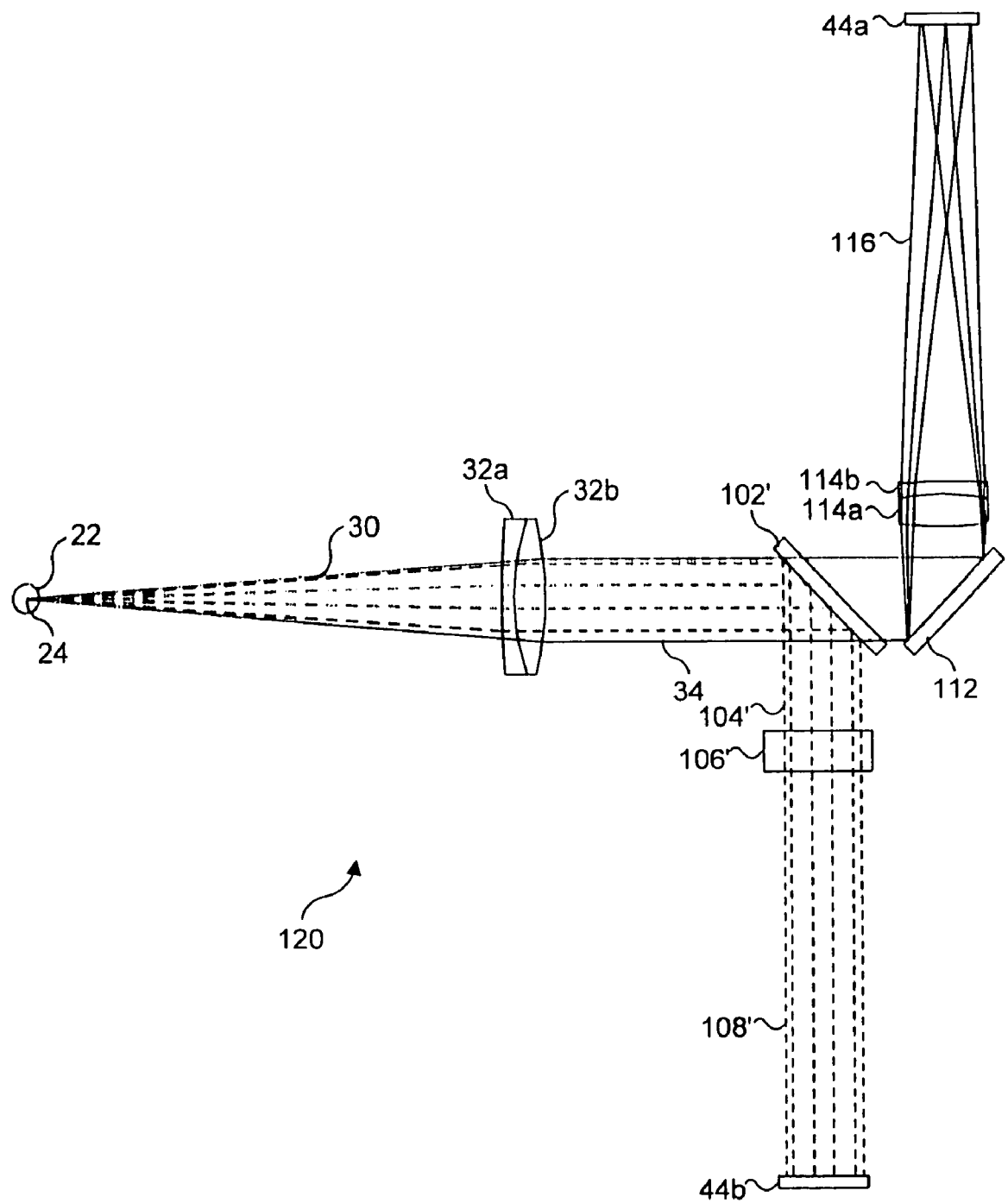
FIG. 10 is a plan view of a still further embodiment in which light forming a scatter patterned image and spectrally dispersed light from the object are imaged by two different TDI detectors.

A sixth preferred embodiment, as illustrated in FIG. 10, is an imaging system 120 that is slightly different than the preceding fifth embodiment, since a dichroic filter 102' is employed that is angled in a different direction, toward a second TDI detector 44b. A dispersed pattern image represented by light 108' is produced by a cylindrical lens 106' in this embodiment. Just as in imaging system 100, light transmitted through dichroic filter 102' is focused onto TDI detector 44a. Aside from using two separate TDI detectors that are disposed at different sides of the imaging system, imaging system 120 is substantially identical in operation to imaging system 100. However, just as in the third preferred embodiment, the use of two separate TDI detectors provides flexibility in the configuration of each leg of the system, including the choice of parameters such as the relative TDI readout rates, axial orientations, inclinations, focal plane positions, and magnification. It should also be noted that imaging system 100 could be constructed to include two separate TDI detectors instead of a single TDI detector, if desired.

Processing of Spectrally Dispersed Images on TDI Detector

When used for cell analysis, the present invention provides substantial utility in resolving FISH spots on the TDI detector, even when the FISH probes are disposed in spatially close relationship within the cell. When spectral imaging occurs in the present invention, the spatial distribution of light in the object is convolved with the spectral distribution of that light to produce the image of the object at the TDI detector. This convolution can result in blurring in the dispersion axis, depending on the spectral bandwidth of the light. Narrow spectral bandwidths will result in little or no blurring depending on the spectral resolution of the system. In the present invention, it is contemplated that the spectral resolution will be approximately 3 nm per pixel, with a spatial resolution in object space of approximately 1 micron. However, the spatial and spectral resolution can be adjusted to match the requirements of the particular application.

Figure 11:
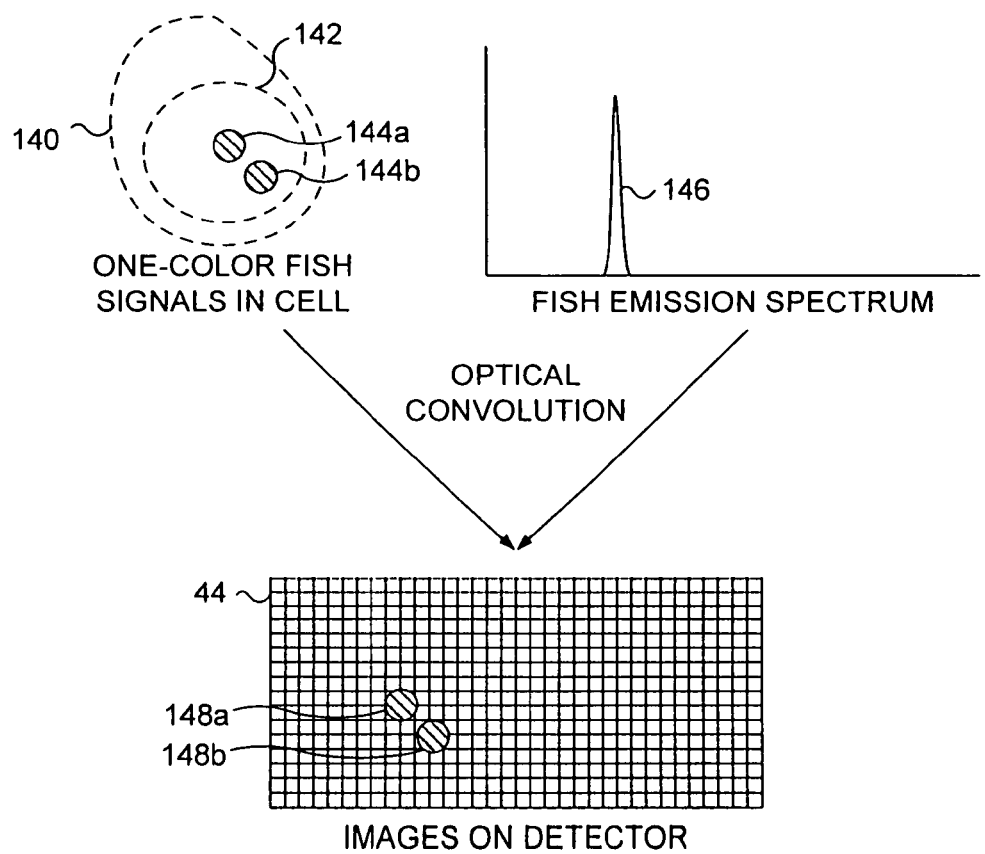
FIG. 11 is a schematic diagram illustrating the optical convolution of a narrow FISH emission spectrum by the present invention, to resolve two FISH probes in a cell.

FIG. 11 illustrates imaging produced using the present invention with a spectral resolution of approximately 10 nm per pixel and a spatial resolution of approximately 0.5 microns. This Figure further illustrates how the present invention is used to image a cell 140 having a nucleus 142 in which are disposed two FISH probes 144a and 144b having the same emission spectrum. In FIG. 11, the emission spectrum 146 of the FISH probes 144a and 144b is approximately 10 nm in width, such as would be produced by "quantum dots" or a narrow-band fluorescent dye. The optical convolution of the narrow bandwidth spectrum results in minimal blurring of FISH spots 148a and 148b, enabling them to be readily resolved on TDI detector 44.

Figure 12:
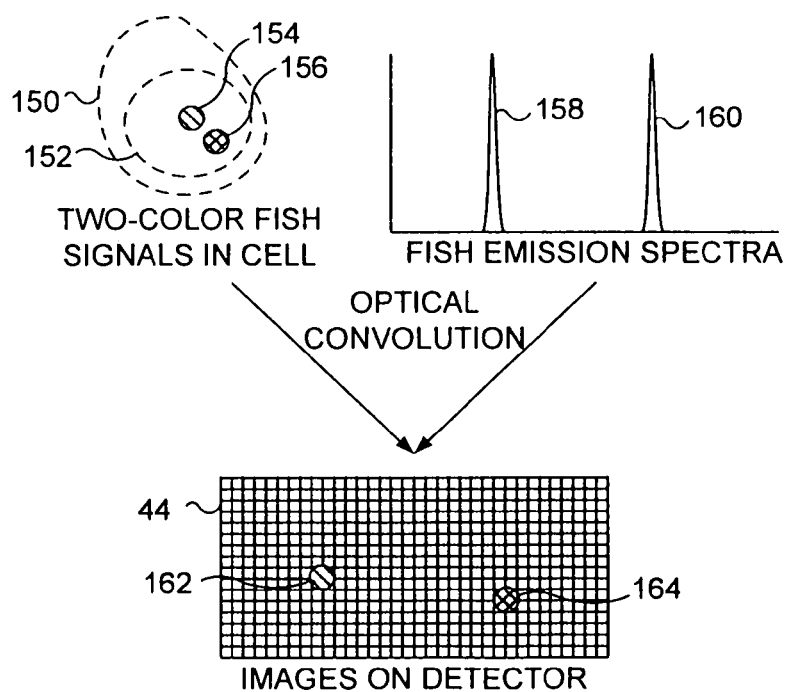
FIG. 12 is a schematic diagram showing the optical convolution of two different colors of narrow FISH emission spectra, to resolve the image of the FISH probes on the TDI detector.

In FIG. 12, a cell 150 is illustrated having a nucleus 152 in which are disposed FISH probes 154 and 156 having different emission spectra. FISH probes are designed so that different emission spectra correspond to different DNA sequences. Each of the emission spectra of FISH probes 154 and 156 are relatively narrow, as indicated by wavebands 158 and 160, and therefore, as in FIG. 11, minimal blurring occurs in FISH spots 162 and 164 when imaged by the present invention. Furthermore, the spectral dispersion of the present invention, which maps wavelength into lateral position on TDI detector 44, produces a relatively wide physical displacement of FISH spots 162 and 164, despite the close proximity of FISH probes 154 and 156 in the cell. Taken together, FIGS. 11 and 12 illustrate how the present invention discriminates FISH probes of the same or different color, thereby enabling the simultaneous enumeration of numerous genetic traits. Those skilled in the art can appreciate that the present invention is well suited to the requirements of fetal cell analysis, where there may be ten or more probes of different colors present in the cell at one time. Furthermore, those skilled in the art will appreciate that the present invention is not limited to the analysis of fetal cells using FISH probes.

Figure 13:
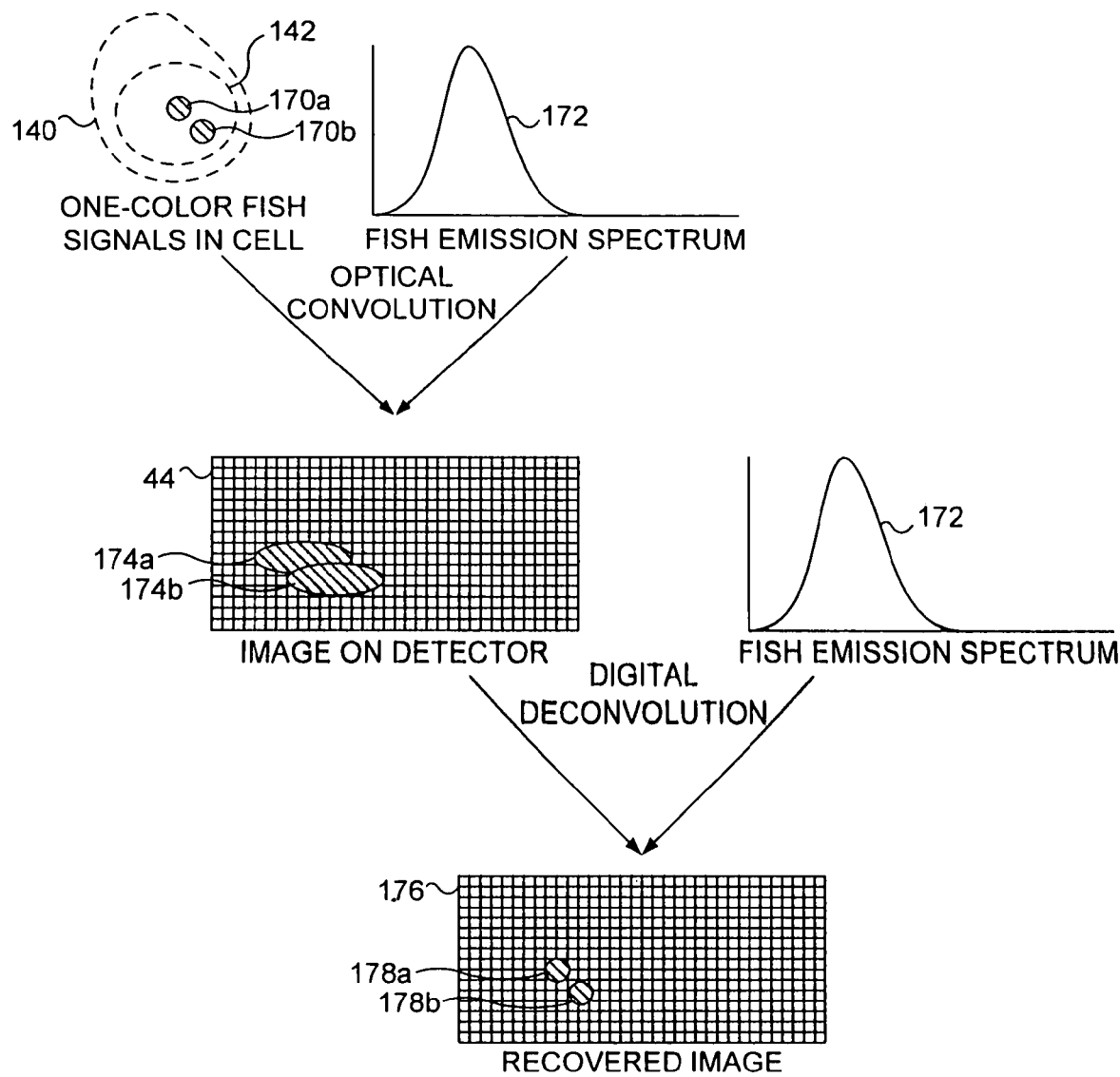
FIG. 13 is a schematic diagram illustrating how for a wider FISH emission spectrum, a deconvolution is provided by the present invention to resolve the image of two FISH probes of a single color.
Figure 14:
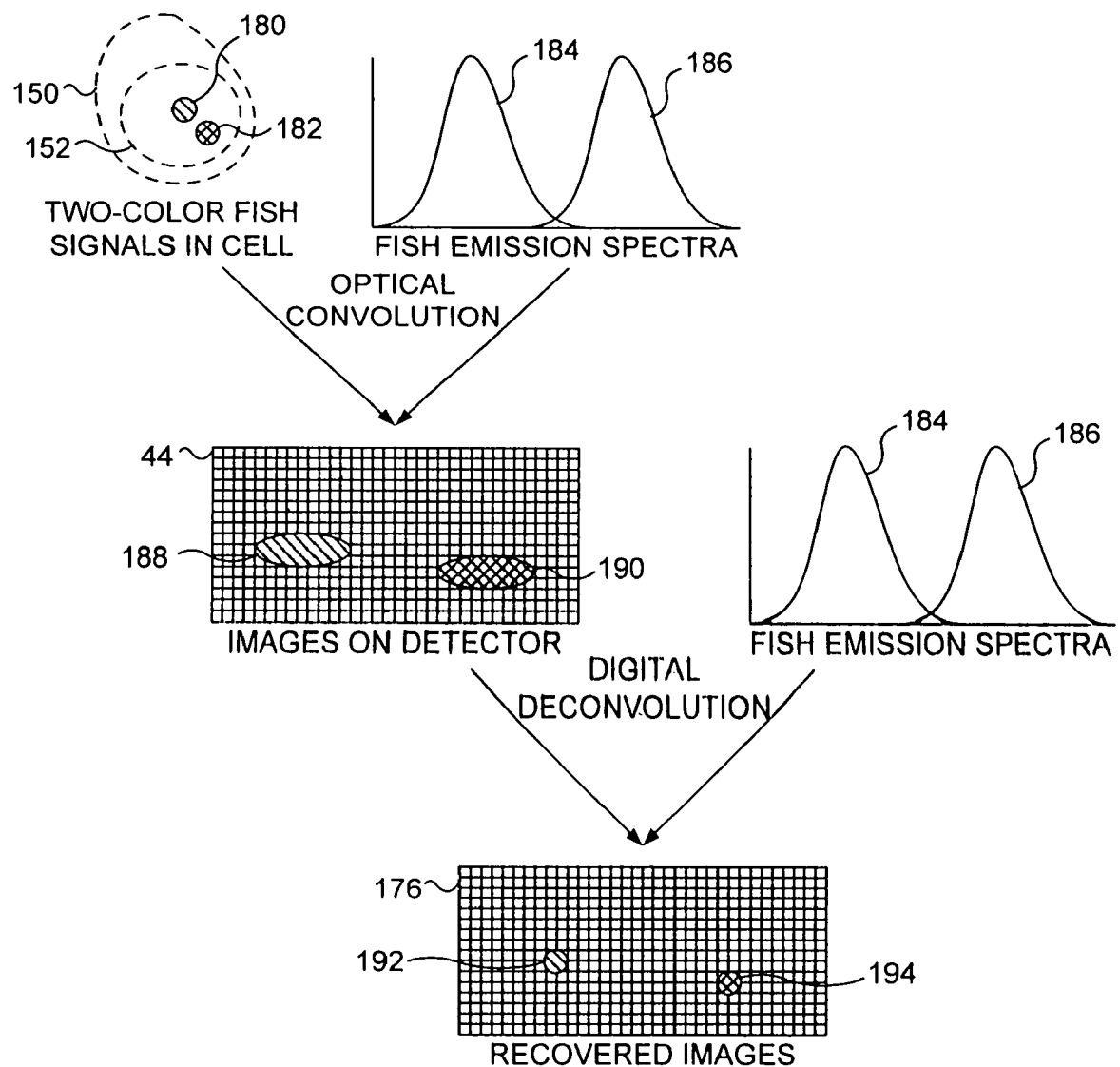
FIG. 14 is a schematic diagram showing the deconvolution of two color FISH spectra that are relatively wide, to resolve the image of the FISH probes.

FIGS. 13 and 14 illustrate images showing that the present invention can also be used with light of wide spectral bandwidth. In this case an additional signal processing step is performed to correct for lateral blurring due to the wide emission spectra. In FIG. 13, a cell 140 having a nucleus 142 is shown, and FISH probes 170a and 170b having a common emission spectrum are disposed in the nucleus. FISH probes 170a and 170b are characterized by producing a relatively wide emission spectrum 172. When optically convolved by the spectral dispersion provided by the present invention, FISH spots 174a and 174b are produced on TDI detector 44, but their images are laterally blurred across TDI detector 44, as a result of their relatively wide emission spectrum. To more clearly resolve the separation of FISH spots 174a and 174b, a deconvolution is carried out on the signal produced by TDI detector 44, with the known FISH emission spectrum, thereby producing accurate FISH spot representations 178a and 178b on a display 176. The deconvolution step enhances the ability of the imaging system to enumerate the number of FISH spots.

FIG. 14 illustrates images showing a corresponding relationship between FISH probes 180 and 182, which are disposed within a nucleus 152 of a cell 150. FISH probes 180 and 182 are characterized by each producing relatively wide band emission spectra 184 and 186, as shown in the Figure. Optical convolution of the fluorescence emitted by the FISH probes, which are spectrally dispersed, produces FISH spots 188 and 190 on TDI detector 44. Again, by deconvolving the known FISH emission spectra with the signal produced by TDI detector 44, the corresponding images shown on display 176 of FISH spots 192 and 194 are recovered by the present invention. Again, the spectral dispersion of the present invention, which maps wavelength into lateral position on TDI detector 44, produces a relatively wide physical displacement of FISH spots 192 and 194, despite the close proximity of FISH probes 180 and 182 in the cell. In this manner, it is possible to resolve these images of FISH spots produced by FISH probes having different and relatively wide emission spectra.

Figure 15:
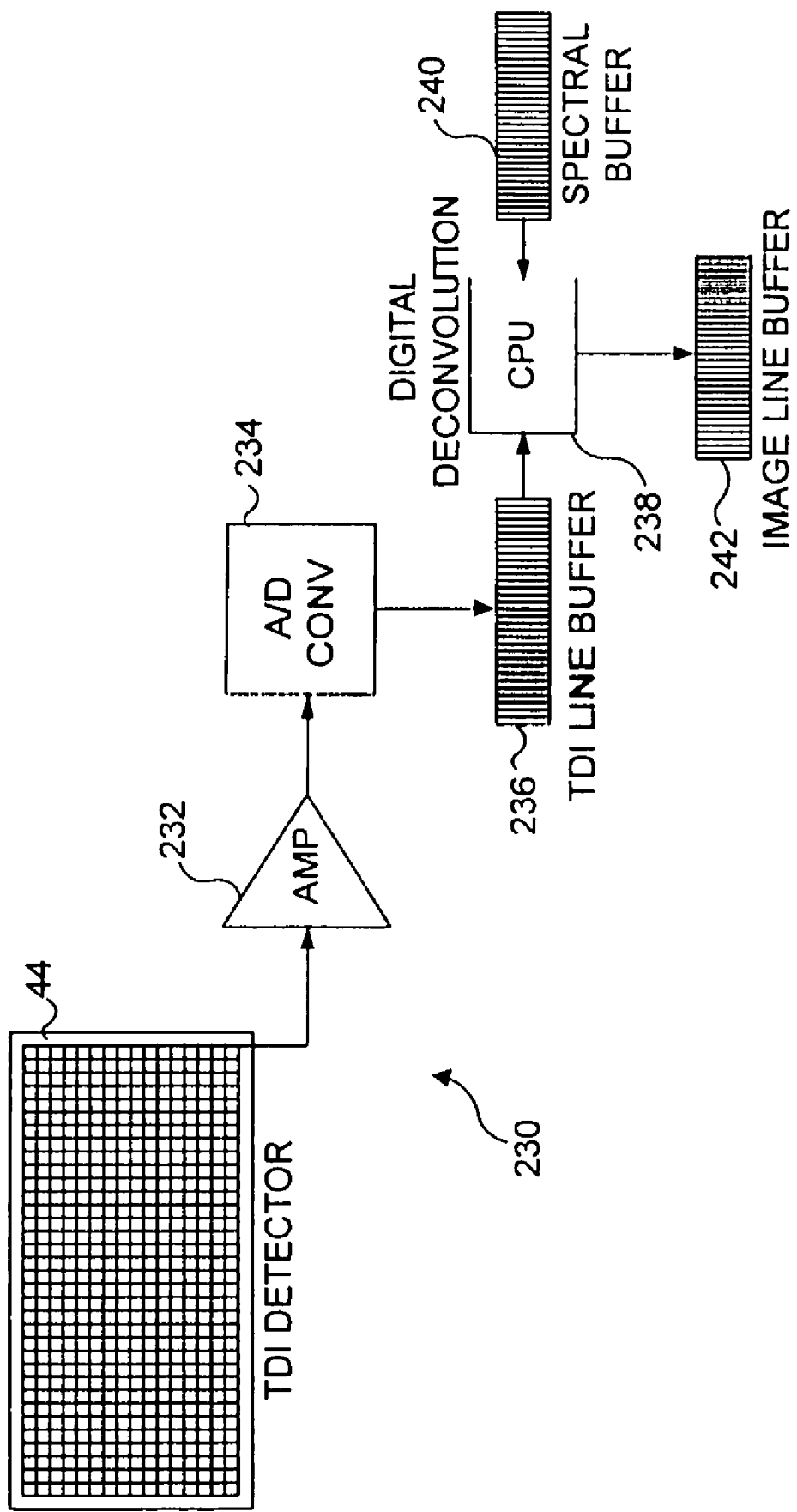
FIG. 15 is a schematic block diagram of the system used to process the signal produced by a TDI detector in the present invention.

A system 230 for analyzing the signal produced by TDI detector 44 and performing the deconvolution steps described above is illustrated in FIG. 15. In this Figure, the signal from TDI detector 44 is applied to an amplifier 232, which buffers the signal and amplifies it to achieve a level required by an analog to digital (A-D) converter 234. This A-D converter converts the analog signal from amplifier 232 into a digital signal that is input into a TDI line buffer 236. TDI line buffer 236 temporarily stores the digital signal until it can be processed by a CPU 238. To carry out the deconvolution noted above, a spectral buffer 240 is loaded with the known emission spectrum for each of the FISH probes being used so that their emission spectra can be deconvolved with the signal stored in TDI line buffer 236. CPU 238 is a high speed processor programmed to carry out the deconvolution and other analysis procedures, enabling the identification of desired characteristics or parameters of the object being imaged. The output from CPU 238 is temporarily stored in an image line buffer 242 that enables the image to be displayed or otherwise recorded for later analysis.

Figure 16:
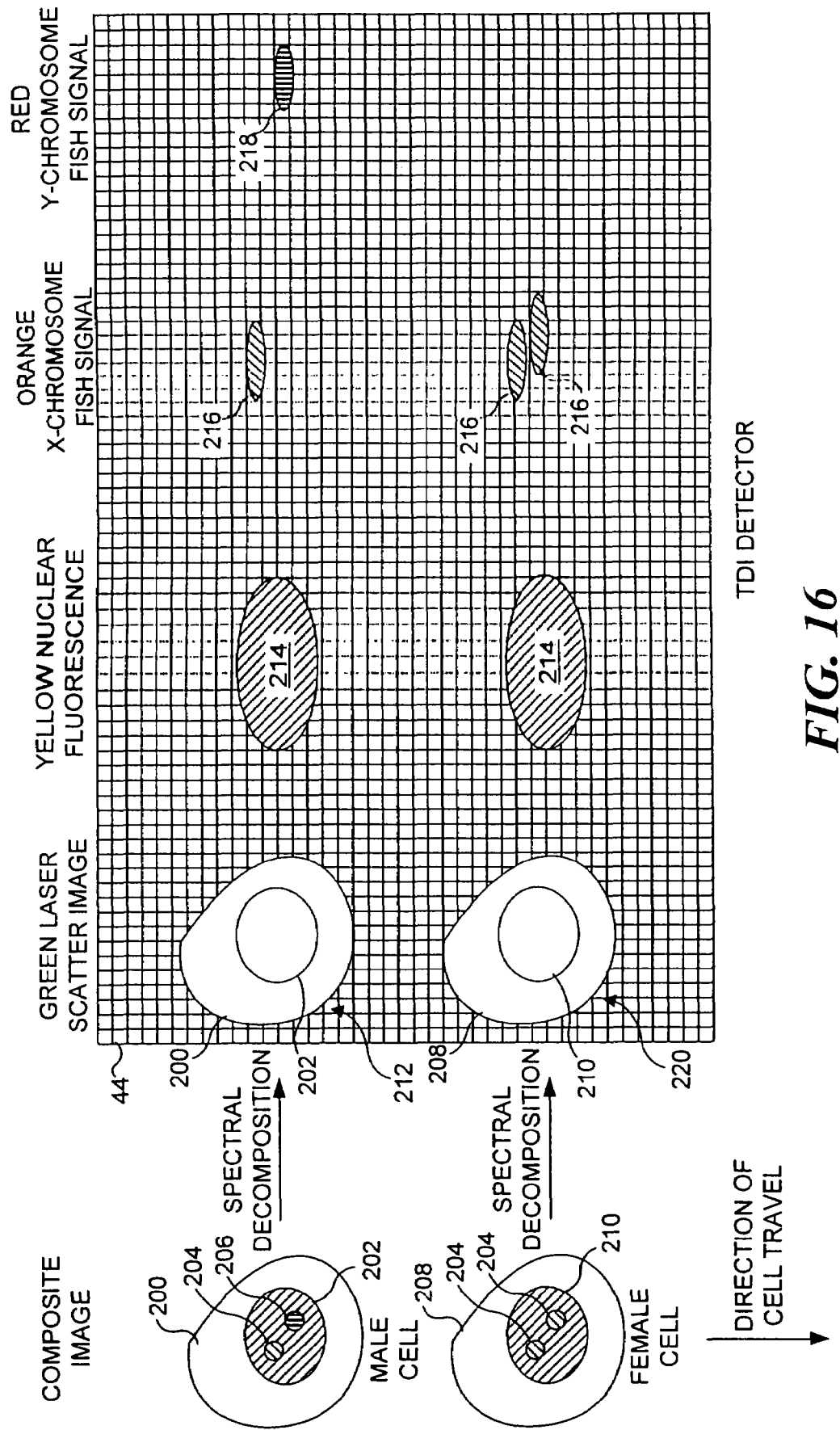
FIG. 16 is a schematic diagram illustrating how the present invention is used to determine whether a cell is from a male or female.

FIG. 16 illustrates a practical application of the present invention for identifying a male cell 200 and a female cell 208 and for producing their corresponding scatter images 212 and 220. Male cell 200 includes a nucleus 202 that has been stained with a yellow fluorescent dye. In addition, a FISH probe 204 produces a fluorescent orange emission, indicating the presence of an X-chromosome in the nucleus, while a FISH probe 206 produces red fluorescence emission, indicating the presence of a Y-chromosome. Spectral decomposition of the fluorescence emissions from male cell 200, when the cell is illuminated with light from a green laser, results in a series of images on TDI detector 44, separated as a function of the wavelength of the light that is imaged. Laser light that is incident on the cells has an extremely narrow waveband, and image 212 of male cell 200 produced by laser scatter is only slightly convoluted by the spectral decomposition process. Green laser scatter image 212 of cell 200 and its nucleus 202 appear on the left side of the TDI detector, while a fluorescent spot 214 corresponding to the yellow fluorescence emitted by nucleus 202 appears in the next few columns on the TDI detector. Furthermore, as a function of the different wavelengths of the fluorescence emitted by FISH probes 204 and 206, FISH spots 216 and 218 appear at locations spaced apart on the detector, but slightly blurred across the columns of TDI detector 44 due to the widths of their respective emission spectra. By analyzing the signals produced by the TDI detector, the FISH probes responsive to X and Y chromosomes are detected, enabling the user to determine that cell 200 is a male cell, since it includes both the X and Y chromosome. Similarly, female cell 208, when spectrally decomposed, also includes the characteristic yellow fluorescence of nucleus 210, but unlike the male cell, includes two FISH spots 216 corresponding to FISH probes 204, which indicates the presence of two X-chromosomes. Because TDI detector 44 also distinguishes the spatial position of male cell 200 and female cell 208, the corresponding spectral decompositions for these cells are readily separately resolved as both cells pass through the imaging system in the direction indicated by the arrow to the lower left of FIG. 16. Again, it should be noted that a deconvolution can be applied to the signal produced by TDI detector 44 to provide better resolution of the corresponding FISH spots that are illustrated.

Non-Distorting Spectral Dispersion Systems

Figure 17:
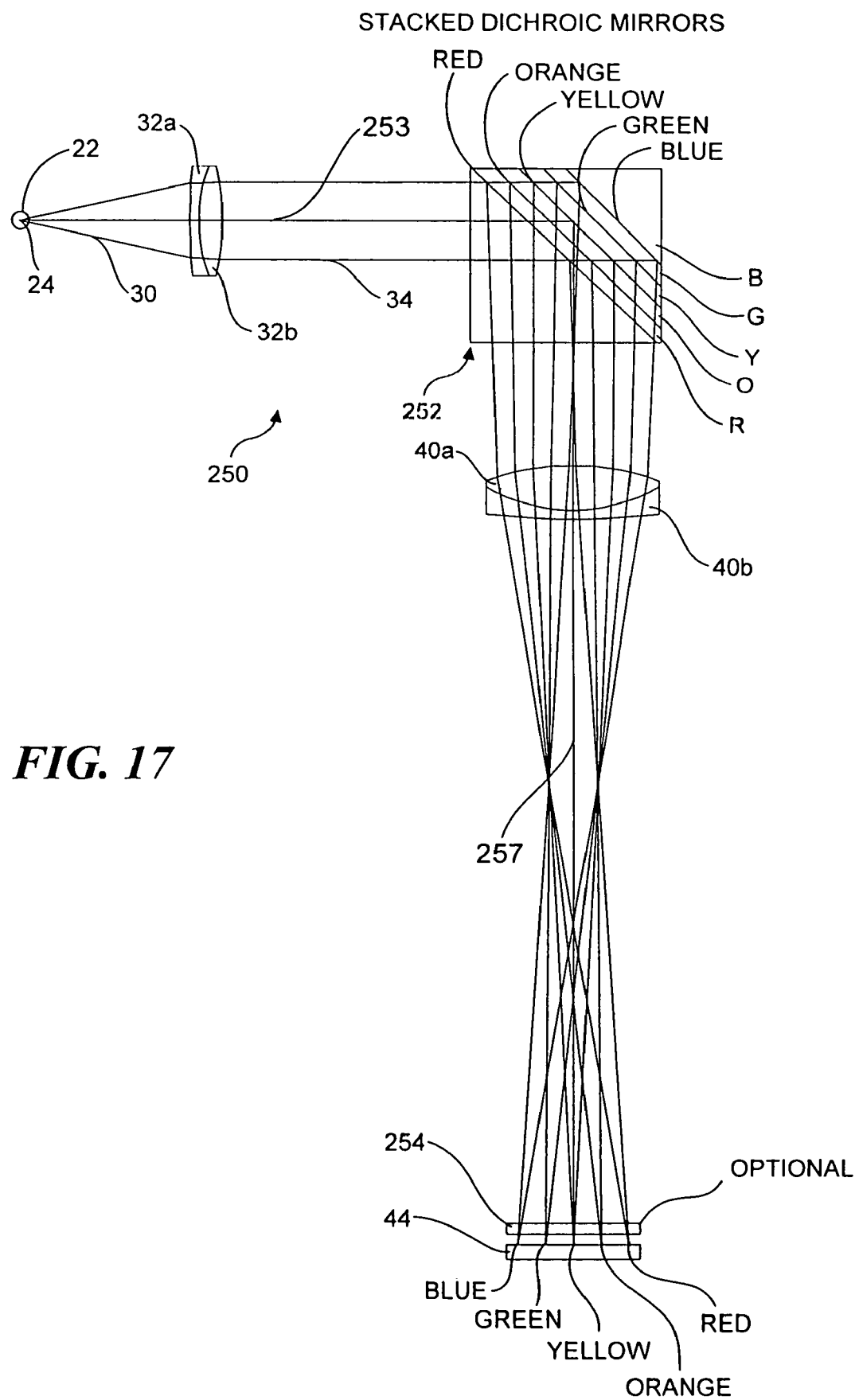
FIG. 17 is a plan view of an alternate embodiment that employs a spectral dispersion component comprising a plurality of stacked dichroic filters used to spectrally separate the light from an object.

The present invention can be provided with a spectral dispersion filter assembly that does not convolve the image with the emission spectra of the light forming the image, thereby eliminating the need for deconvolution of the emission spectra from the image. FIG. 17 illustrates a seventh preferred embodiment of the invention corresponding to such a non-distorting spectral dispersion system 250 that employs a five color stacked wedge spectral dispersing filter assembly 252. This seventh embodiment is substantially similar to the embodiment shown in FIGS. 1, 2, and 3, except that spectral dispersing prism element 36 (of FIGS. 1, 2 and 3) is replaced by spectral dispersing filter assembly 252. The spectral dispersing filter assembly splits the light into a plurality of light beams having different bandwidths. Each light beam thus produced is directed at a different nominal angle so as to fall upon a different region of TDI detector 44. The nominal angular separation between each bandwidth produced by the spectral dispersing filter assembly 252 exceeds the field angle of the imaging system in object space thereby preventing overlap of the field images of various bandwidths on the detector.

Figure 18:
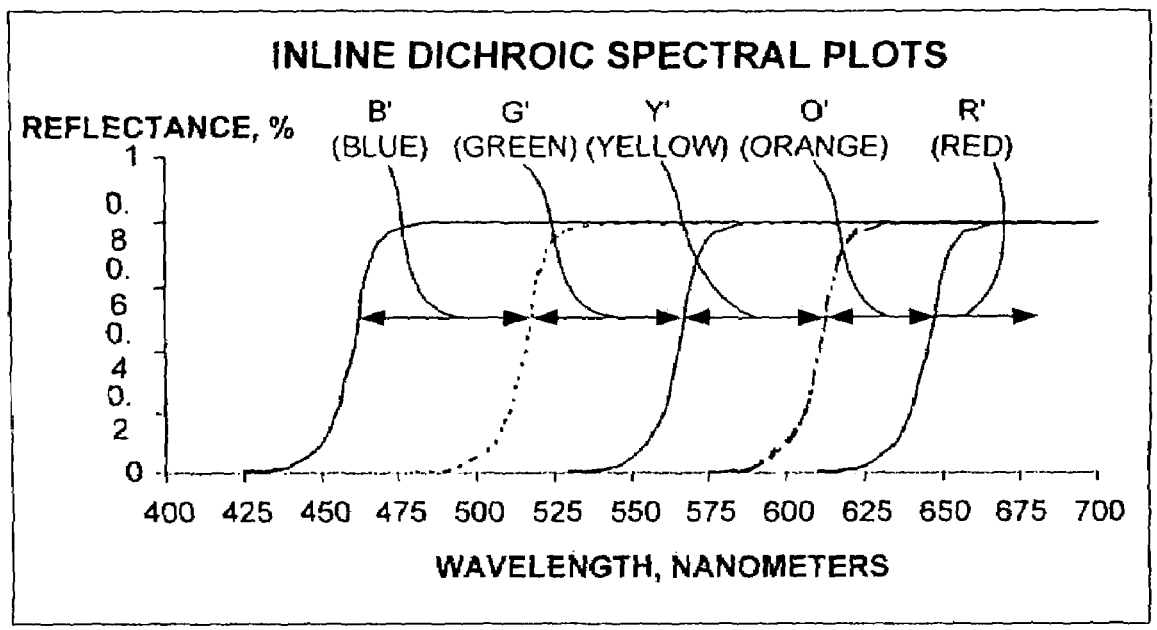
FIG. 18 is an X-Y plot of several typical passbands for the dichroic filters employed in the embodiment shown in FIG. 17.

Spectral dispersing filter assembly 252 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 34, oriented at an angle of approximately 44.0° relative to an optic axis 253 of collection lenses 32a and 32b. Light of red wavelengths and above, i.e., >640 nm, is reflected from the surface of red dichroic filter R at a nominal angle of 1°, measured counter-clockwise from a vertical optic axis 257. Exemplary spectral reflectance characteristics R' of red dichroic filter R are plotted in FIG. 18, along with exemplary spectral reflectance characteristics corresponding to the other dichroic filters used in spectral dispersing filter assembly 252. In FIG. 18, O' indicates the spectral reflectance characteristics of orange dichroic filter O, Y' indicates the spectral reflectance characteristics of yellow dichroic filter Y, etc. The light reflected by red dichroic filter R leaves spectral dispersing filter assembly 252 and passes through imaging lenses 40a and 40b, which cause the light to be imaged onto a red light receiving region of TDI detector 44, which is disposed toward the right end of the TDI detector, as shown in FIG. 17.

Orange dichroic filter O is disposed a short distance behind red dichroic filter R and is oriented at an angle of 44.5 degrees with respect to optic axis 253. Light of orange wavelengths and greater, i.e., >610 nm, is reflected by orange dichroic filter O at a nominal angle of 0.5° with respect to vertical optic axis 257. Because the portion of collected light 34 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 257, and is imaged by imaging lenses 40a and 40b so as to fall onto an orange light receiving region disposed toward the right hand side of TDI detector 44 between a center region of the TDI detector and the red light receiving region, again as shown in FIG. 17.

Yellow dichroic filter Y is disposed a short distance behind orange dichroic filter O and is oriented at an angle of 45° with respect to optic axis 253. Light of yellow wavelengths, i.e., 560 nm and longer, is reflected from yellow dichroic filter Y at a nominal angle of 0.0° with respect to vertical optic axis 257. Wavelengths of light reflected by yellow dichroic filter Y are effectively bandpassed in the yellow region between 560 nm and 610 nm and are imaged by imaging lenses 40a and 40b near vertical optic axis 257 so as to fall on a yellow light receiving region toward the center of TDI detector 44.

In a manner similar to dichroic filters R, O, and Y, dichroic filters G and B are configured and oriented so as to image green and blue light wavebands onto respective green and blue light receiving regions of TDI detector 44, which are disposed toward the left-hand side of the TDI detector. By stacking the dichroic filters at different predefined angles, spectral dispersing filter assembly 252 collectively works to focus light within predefined wavebands of the light spectrum onto predefined regions of TDI detector 44. Those of ordinary skill in the art will appreciate that the filters used in the spectral dispersing filter assembly 252 may have spectral characteristics that differ from those described above and shown in FIG. 18. Further, the spectral characteristics may be arbitrary and not limited to dichroic in order to achieve the desired dispersion characteristics.

The wedge shape of the dichroic filters in the preceding discussion allows the filters to be placed in near contact, in contact, or possibly cemented together to form the spectral dispersing filter assembly 252. The angle of the wedge shape fabricated into the substrate for the dichroic filter enables easy assembly of the spectral dispersing filter assembly 252, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 252. In this case another means such as mechanically mounting the filters could be used to maintain the angular relationships between the filters.

Figure 19:
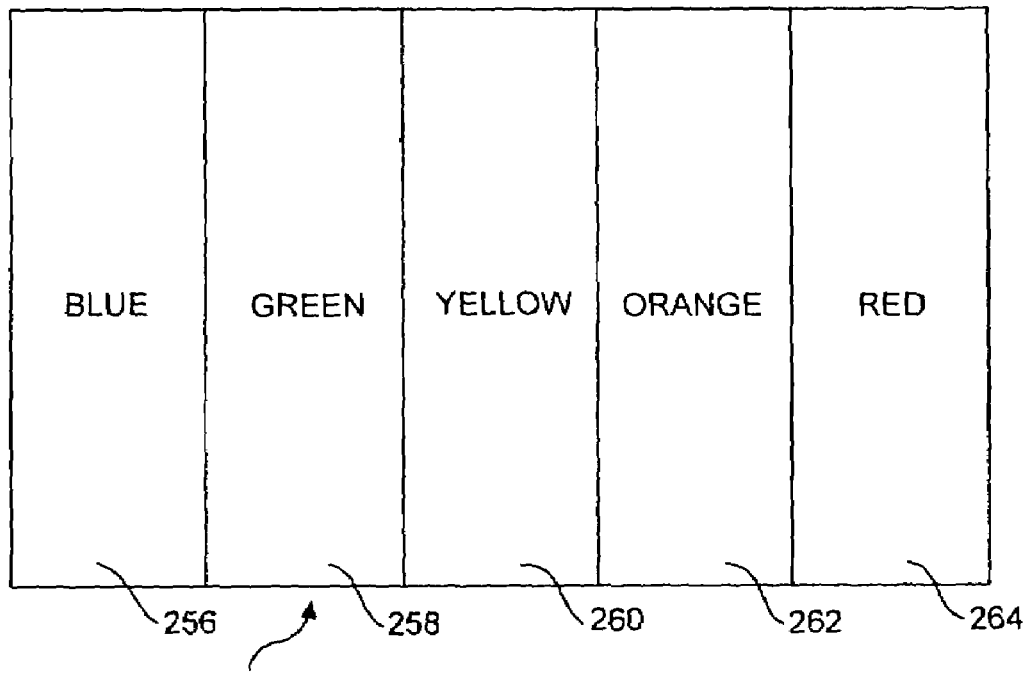
FIG. 19 is a schematic illustration of a detection filter assembly that may optionally be placed in front of the TDI detector in the embodiment of FIG. 17, to further suppress out-of-band light.
Figure 20A:
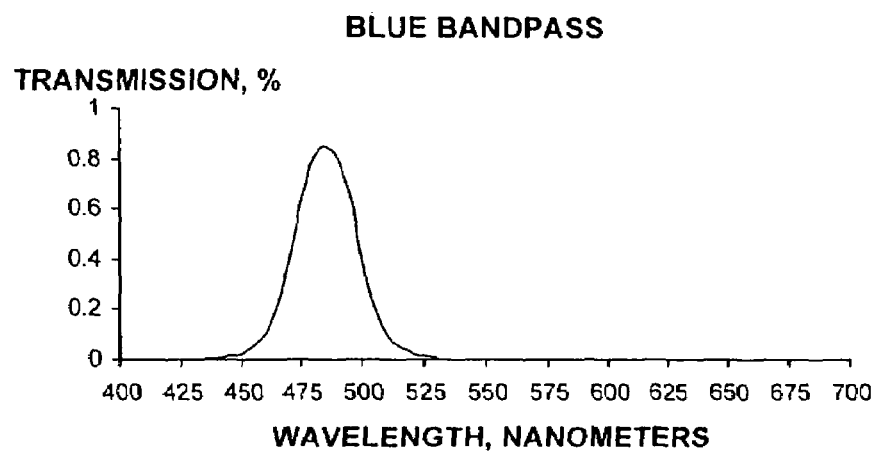
FIGS. 20A-20E are X-Y plots of transmission vs. wavelength for corresponding passbands of the filter segments of the detection filter assembly that may optionally be placed in front of the TDI detector.
Figure 20B:
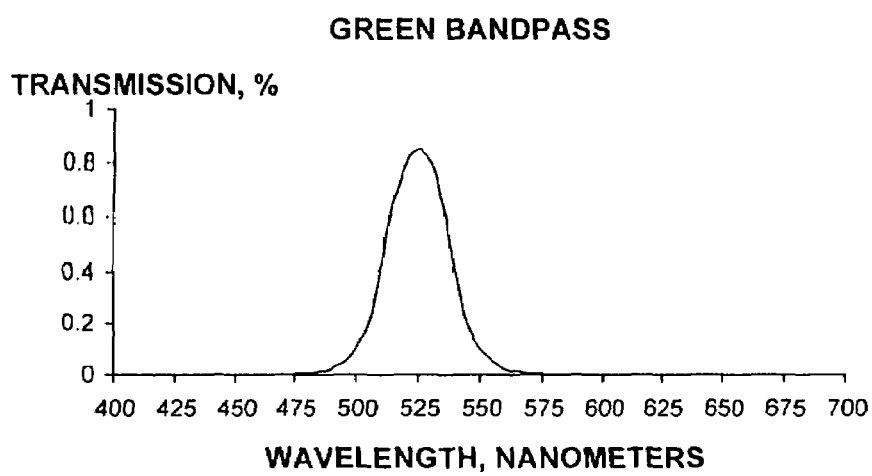
Figure 20C:
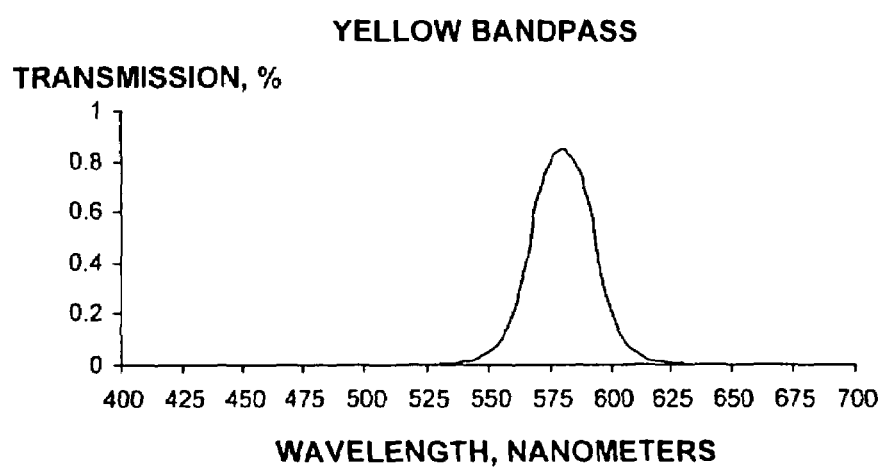
Figure 20D:
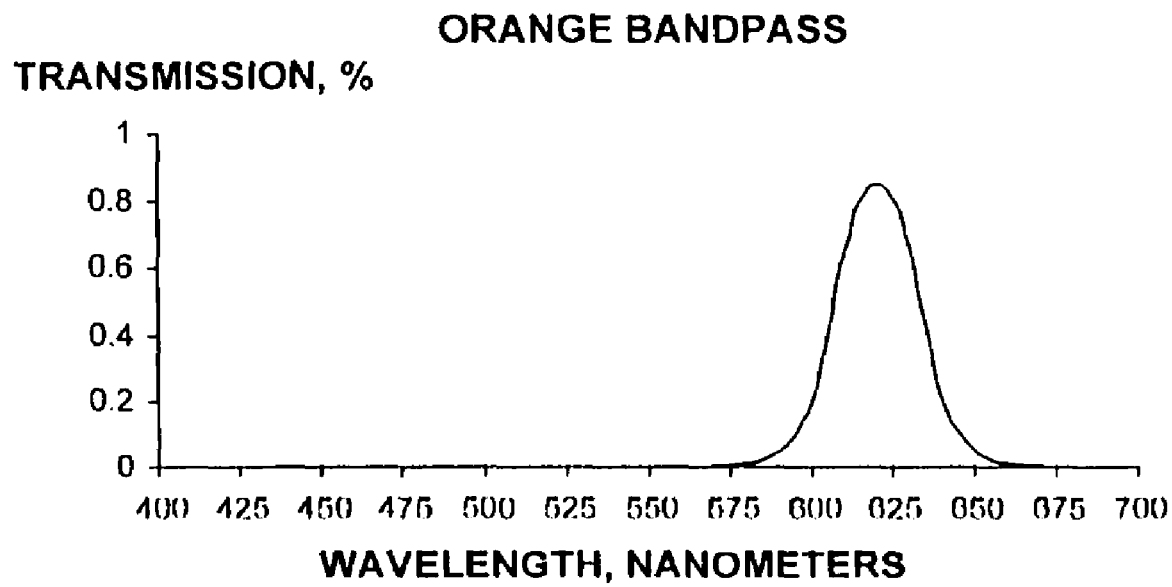
Figure 20E:
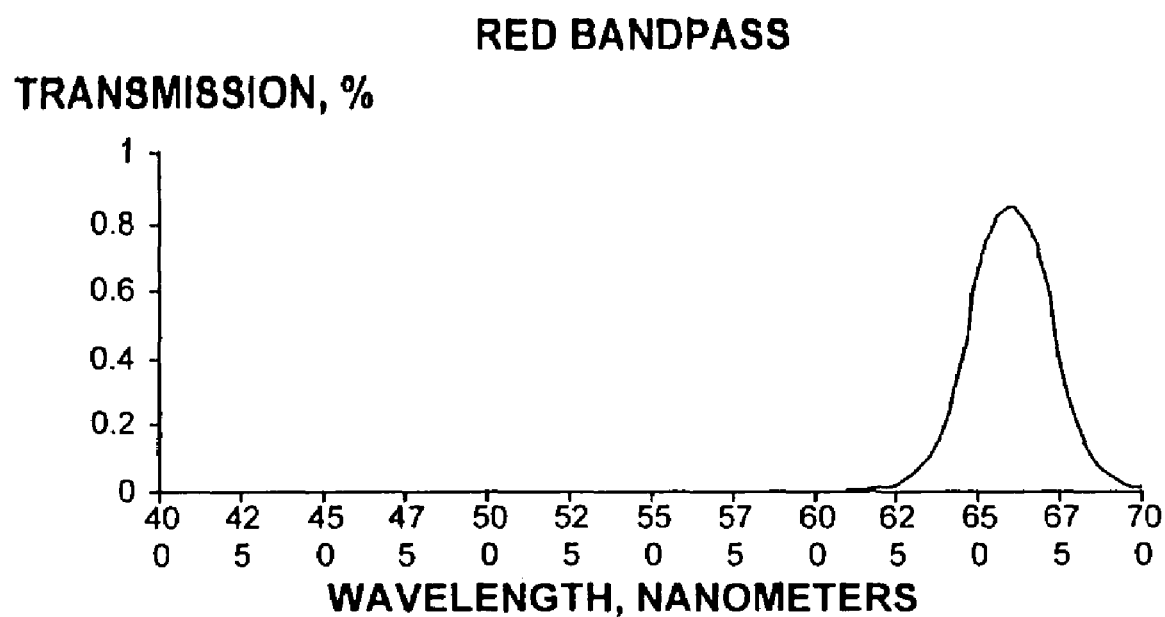

In addition to the foregoing configuration, non-distorting spectral dispersion system 250 may optionally include a detector filter assembly 254 to further attenuate undesired signals in each of the light beams, depending upon the amount of rejection required for out-of-band signals. FIG. 19 illustrates the construction of an exemplary detector filter 254 corresponding to the five color bands discussed above and includes a blue spectral region 256, a green spectral region 258, a yellow spectral region 260, an orange spectral region 262, and a red spectral region 264, all of which are disposed side-by-side, as shown in the Figure. The corresponding spectral characteristics of the blue, green, yellow, orange, and red spectral regions or wavebands are respectively shown in FIGS. 20A-20E. The detection filter assembly shown in FIG. 19 may be constructed by cementing separate filters in side-by-side arrangement on a common substrate or by other means well known to those or ordinary skill in the art. Additionally, the ordinary practitioner in the art will understand that the filter may alternatively be placed at an intermediate image plane, instead of directly in front of TDI detector 44.

In the embodiment shown in FIG. 17, light may pass through each dichroic filter in the spectral dispersing filter assembly 252 twice before exiting spectral dispersing filter assembly 252. This condition will further attenuate out-of-band signals, but will also attenuate in-band signals.

Figure 21:
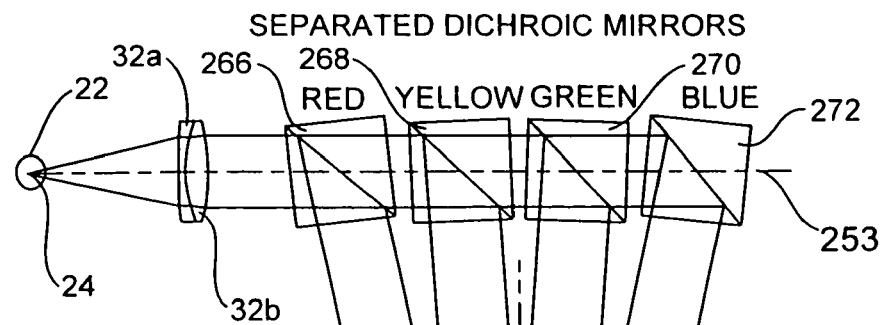
FIG. 21 is a plan view of another embodiment of the configuration of FIG. 17, wherein the spectral dispersion filter system comprises a plurality of dichroic cube filters orientated at various angles to provide the spectral dispersion function.
Figure 21:
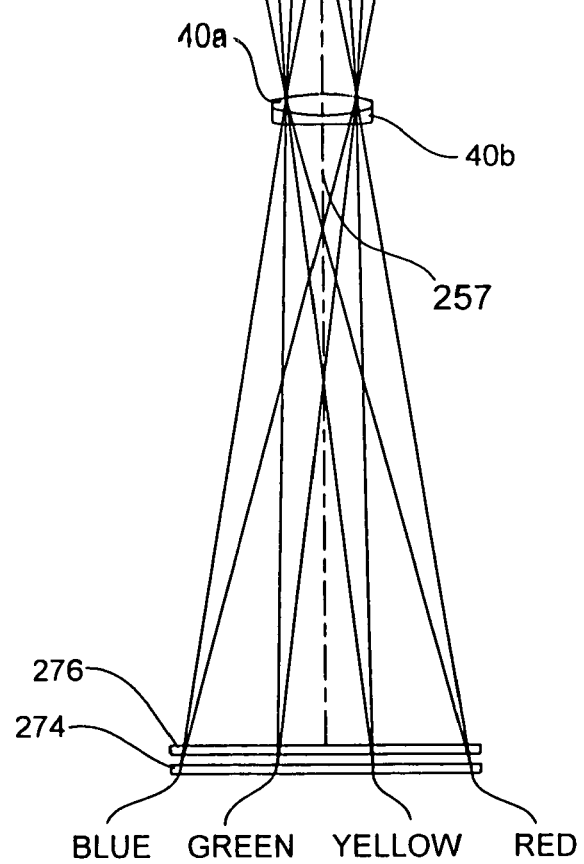

FIG. 21 illustrates an eighth embodiment of the present invention in which the light does not pass through another dichroic filter after reflection. In this embodiment, a plurality of cube dichroic filters, including a red cube filter 266, a yellow cube filter 268, a green cube filter 270, and a blue cube filter 272 are spaced apart sufficiently to ensure that light does not pass through any of the cube filters more than once. Like the embodiment of FIG. 17, the cube dichroic filters are oriented at appropriate angles to image light within a predefined bandwidth to distinct regions on a TDI detector 274. As the light is reflected from each of cube dichroic filters 266, 268, 270 and 272, it is directed toward imaging lenses 40a and 40b, and different bandpass portions of the light are focused upon corresponding red, yellow, green, and blue light receiving segments or regions defined on a light receiving surface of TDI detector 274. If desired, an optional detector filter assembly 276 of similar construction to detector filter assembly 254 (but without the orange spectral region) may be used to increase the rejection of out-of-band signals. It should be apparent to those skilled in the art that separate spaced apart plate, or pellical elements could also be used in this application instead of the cube filters. In the eighth embodiment illustrated in FIG. 21, image lenses 40a and 40b must be placed a sufficient distance away from the plurality of cube filters to minimize the clear aperture requirement for lenses 40a and 40b. Those skilled in the art will appreciate the clear aperture in the plane orthogonal to the page can increase as the distance between the lenses and plurality cube filters increases. Therefore, the placement of lenses 40a and 40b must be chosen to appropriately accommodate the clear aperture in both planes.

The foregoing descriptions of the seventh and eighth embodiments illustrate the use of four and five color systems. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and or bandpass filters that are used. It will be appreciated that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axis of the system. Finally, it should be apparent that dispersion of the collected light may be performed on the basis of non-spectral characteristics, including angle, position, polarization, phase, or other optical properties.

As with the embodiments discussed above, many applications of the seventh and eighth embodiments will require that one or more light sources be used to provide light that is incident on the object being imaged. Accordingly, various light sources disposed at different positions, such as those shown in FIGS. 5-7 and discussed above, may be used to enhance the image quality produced by each of these embodiments. For clarity and to simplify the explanation of these embodiments, the light sources have been omitted in FIGS. 17 and 21; however, it will be recognized by those skilled in the art how such light sources may be employed in these embodiments, based on the previous discussion of the use of the light sources with respect to other embodiments.

Figure 22:
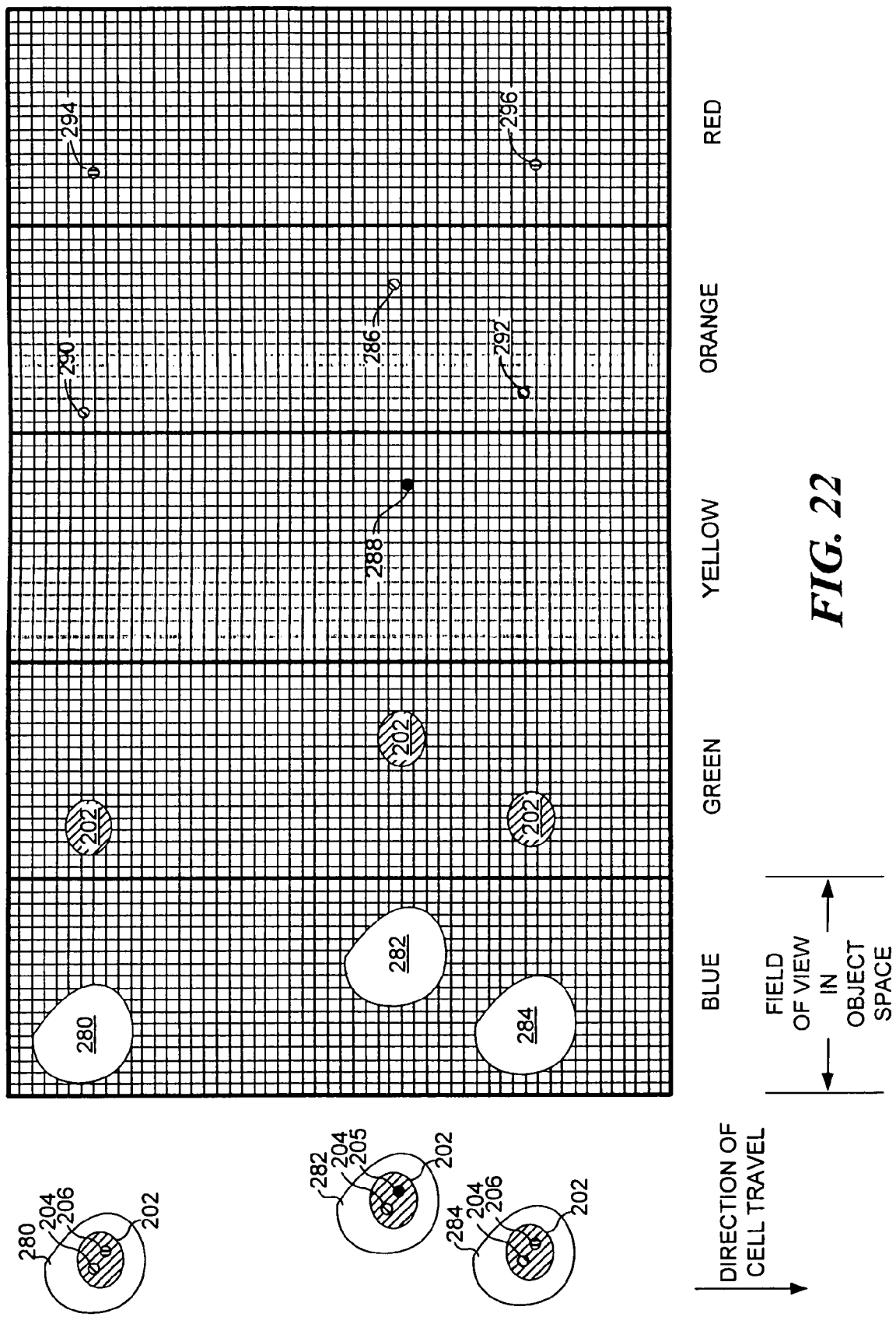
FIG. 22 illustrates an exemplary set of images projected onto the TDI detector when using the spectral dispersing filter system of the FIG. 17.

FIG. 22 illustrates the distribution of images on TDI detector 44 corresponding to imaging a plurality of cells 200 when using non-distorting spectral dispersion system 250. As will be evident by comparing FIG. 22 to FIG. 16, the resultant images on the TDI detector are similar in many ways. However, when using the non-distorting spectral dispersion system, there is no image broadening as is seen in FIG. 22, which would otherwise result due to the convolution of the emission spectrum and the object. Instead, all wavelengths within the predefined bandwidth of each dichroic filter are reflected from the filter at the same nominal angle, so image components that fall within that passband suffer no positional distortion on the detector. The field angle orthogonal to flow in object space is also indicated on FIG. 22. In this particular configuration, the field angle in object space is less than +/− 0.25°. Those skilled in the art will appreciate that the field angle can be made larger or smaller.

Figure 25:
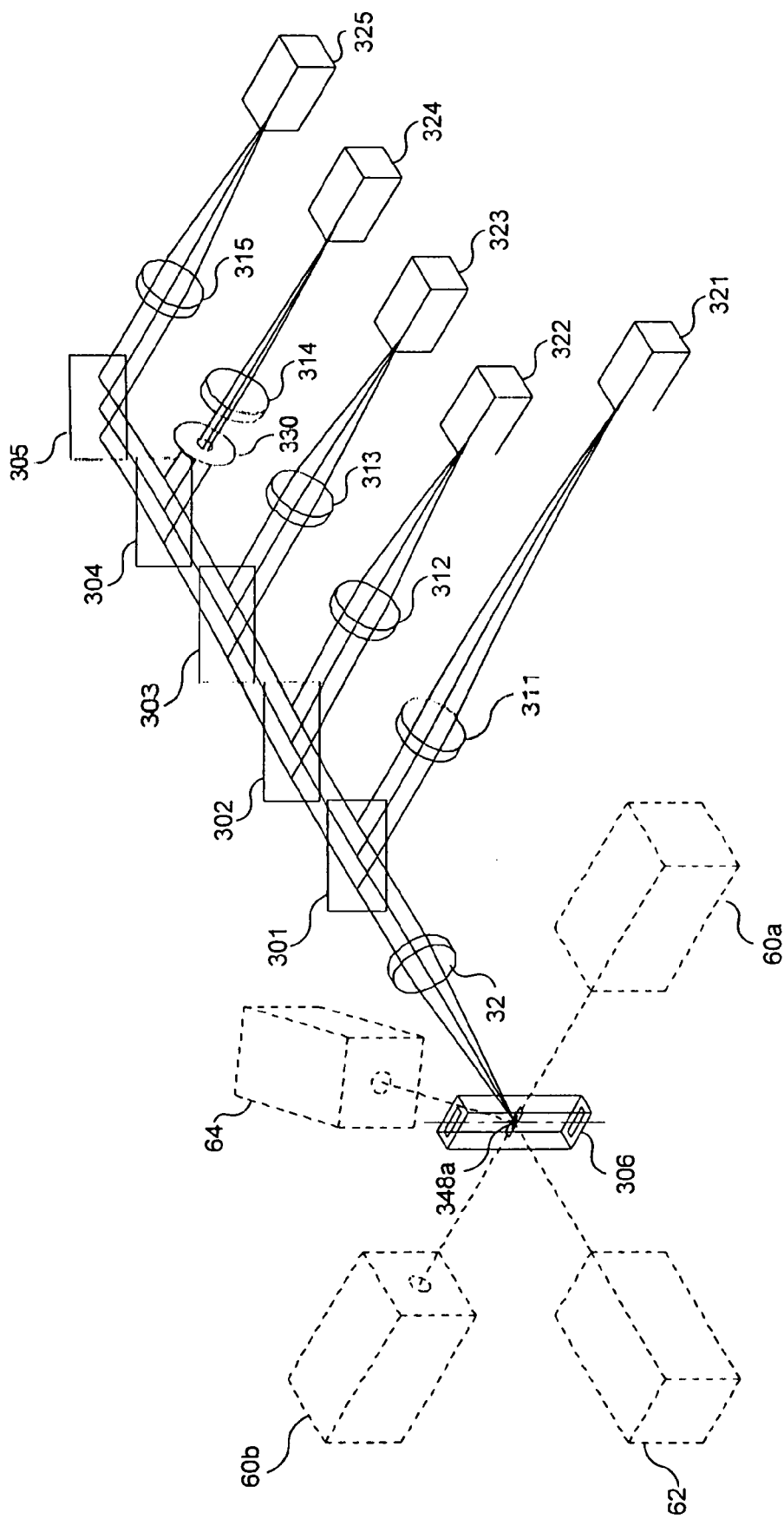
FIG. 25 is an isometric view of an alternate embodiment, employing separate TDI detectors and separate imaging lenses for each spectrally decomposed image.

To the extent that the field angle is made larger, for example, to image cells over a wider region on a slide or in a broad flat flow, the field angle at the detector will increase in proportion to the number of colors used. Broad flat flow can easily be created using commercially available flow cells, as shown in FIG. 25, which includes a flow cell 306. Flow cell 306 has a cross section that is elongated along an axis that is perpendicular to both the flow and optical axes. The generation of a broad flat flow is discussed in many references, including U.S. Pat. No. 5,422,712. Use of flow cell 306 enables a broad flat flow to readily be achieved. In embodiments that include flow cell 306 or other means to provide a broad flat flow, the field angle is preferably increased by an amount that is sufficient to enable any objects entrained in the broad flat flow to be imaged and the resulting image to be captured by a detector. Thus, as the width of a flow volume increases, the field angle must also increase in a proportional fashion, to ensure that all objects in that flow volume can be imaged as they pass through the field of view.

FIG. 22 illustrates the image projected onto the detector when three cells 280, 282, and 284 are passing through the field of view. Light scatter images of cells 280, 282, and 284 are seen on the left side of the detector, which is denoted as the BLUE area. Images of cell nuclei 202 stained with a green fluorescent dye are evident in the GREEN area of the detector. Three differently-colored genetic probes 204, 205, and 206 are also employed for the analysis of the sex chromosomes within the cells. Probe 204 stains the X chromosome with an orange fluorescing dye, probe 205 stains the Y chromosome with yellow fluorescing dye, and probe 206 stains the inactive X chromosome in female cells with a red fluorescing dye. Cell 282 is imaged onto the detector as shown in FIG. 22. An image 286 of probe 204 from cell 282 is seen in the ORANGE area of the detector. Likewise, an image 288 of probe 205 is seen in the YELLOW area of the detector. The signal on the detector is processed to determine the existence and position of these images on the detector to determine that cell 282 is a male cell. In a similar manner, cells 280 and 284 contain probes 204 and 206, which are indicated in images 290 and 292 in the ORANGE area of the detector, and images 294 and 296 in the RED area of the detector, respectively, indicating that these cells are female.

Multiple TDI Detector Embodiments of Non-Distorting Spectral Dispersing Systems

Figure 26:
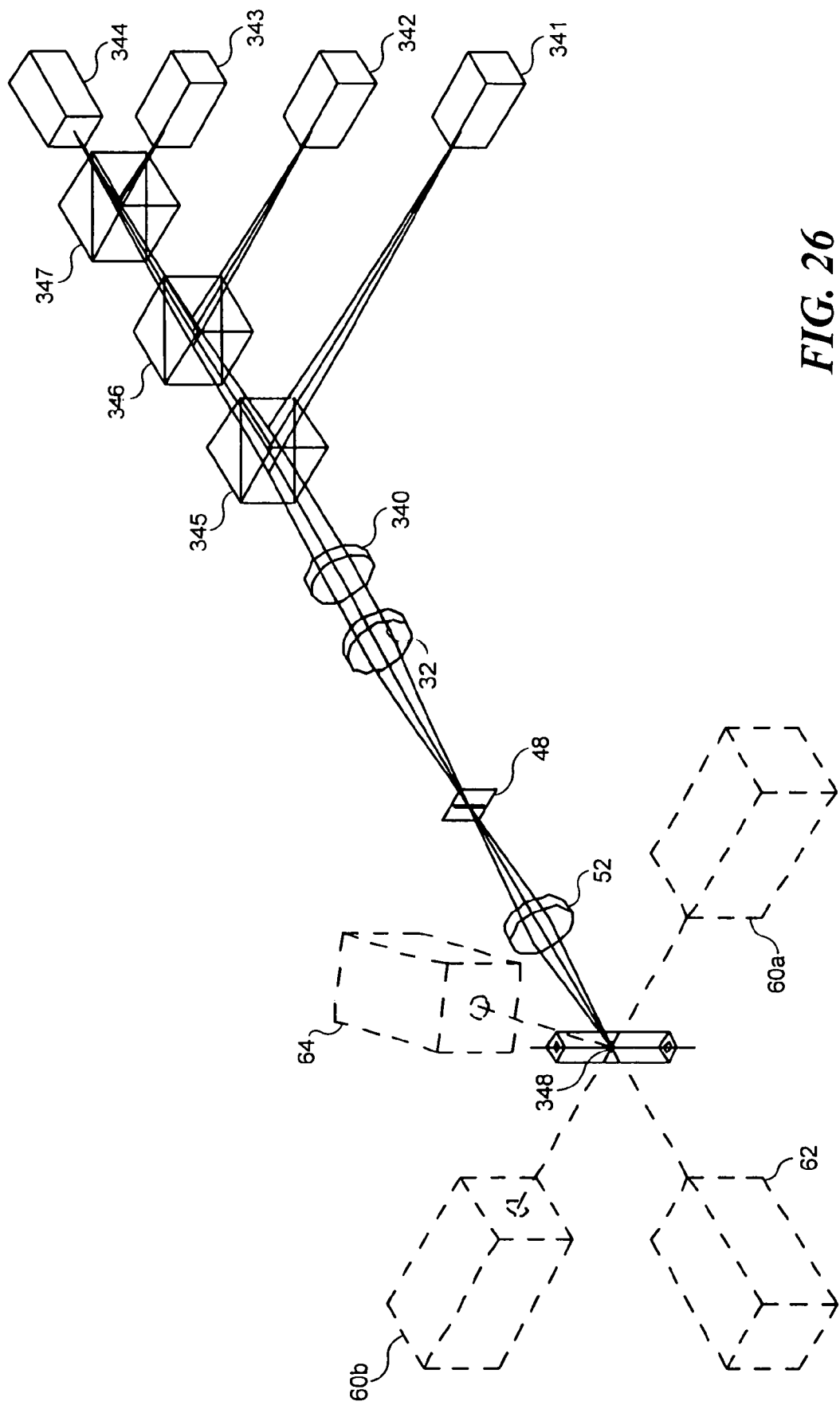
FIG. 26 is an isometric view of an alternate embodiment employing separate TDI detectors, with a common imaging lens placed prior to the spectral decomposition elements.

Other embodiments of the present invention that employ multiple detectors for spectral dispersing and imaging are illustrated in FIGS. 25, 26, and 28. Spectral decomposition is implemented using dichroic filters, generally as described above. However, as illustrated in FIG. 25, separate imaging lenses and detectors are used for each spectral region. Dichroic filters 301-305 are disposed in infinite space with respect to the object from which light is being spectrally decomposed to minimize optical aberrations. After each dichroic filter, separate imaging lenses 311-315 are used to form an image of the object on corresponding detectors 321-325. In this configuration, each detector has fewer pixels than in the embodiments described above, enabling the present embodiments to operate at high pixel line rates. The images projected on each detector appear as shown on one zone of the detector illustrated in FIG. 17. The images on the detector configured to receive light in the red portion of the spectrum appear like those in the right-most zone of FIG. 17.

The embodiments shown in FIGS. 25, 26, and 28 have an advantage in optical efficiency over other embodiments, because the light from the object only passes through each dichroic filter once. A further advantage of the multiple detector embodiments is that each detector can be focused independently for each color, thereby simplifying the optical design by removing constraints on longitudinal color correction. A still further advantage is that the quantum efficiency of each detector can be individually optimized for its particular color band. Those of ordinary skill in the art will readily recognize that such optimization can be accomplished through doping of the semiconductor materials utilized in the detector. When multiple imaging lenses are employed, as shown in FIG. 25, one or more lenses (as exemplified by lens 311), may have a different focal length, thereby enabling simultaneous image collection with different magnifications. In this case, the clock rate on detector 321 will be proportionally higher to maintain synchronization with the moving image, which is expected to be useful when one channel is used with a higher magnification for brightfield image collection, to more accurately analyze morphological detail. The configuration shown in FIG. 25 also enables channel independent control of numerical aperture, as illustrated by the disposition of optional aperture stop 330. It should be noted that an object plane 348a as shown in FIG. 25 is larger than object planes 348 illustrated in other Figures, due to the characteristics of flow cell 306. As noted above, flow cell 306 enables a broad flat flow to be achieved, such that multiple objects simultaneously passing through object plane 348a can be imaged simultaneously, as long as each image covers a sufficiently large field angle. When the present invention is used in conjunction with such a broad flat flow, the field angle needs to be matched to the size of the object plane (such as object plane 348a) so that the images produced encompass substantially all of the object plane. Note that the object plane is defined by the perimeter of the fluid channel employed.

FIG. 26 illustrates another embodiment of the multiple detector approach. While similar to the embodiment illustrated in FIG. 25, the embodiment of FIG. 26 has the advantage of reducing the number of imaging lenses required to project an image on the detectors. In the embodiment of FIG. 26, an image lens 340 is placed before dichroic filters 345-347. Those skilled in the art will appreciate that the functions of collection lens 32 and image lens 340 can be carried out by a single element. Detectors 341-344 are placed at the appropriate positions along the optical path to image an object plane 348 on the surface of each detector. Detectors 341-343 are placed in a path of light from the object that is reflected from dichroic filters 345, 346, and 347, while detector 344 is placed in the path of light from the object that is transmitted through dichroic filter 347. The filters are disposed in convergent space with respect to the image of the object and therefore, each filter, depending upon its design, may impart astigmatism, coma, spherical, and chromatic aberration to the images at each downstream detector. Progressively, more of these aberrations are added by each subsequent filter. In a typical implementation of the present invention, the numerical aperture (i.e., the product of the index of refraction and the sine of the half cone angle of illumination) in the filter space is approximately 0.03. Therefore, if cube substrates are employed for the dichroic filters, coma and astigmatism are negligible, while spherical aberration is substantially eliminated, being less than 0.15 waves peak. Longitudinal chromatic aberration is effectively canceled by moving the detectors to the plane of best focus for their respective color band. Pellicles can also be used in place of the cubes for the substrates of the dichroic filters, with excellent theoretical optical performance.

Figure 27:
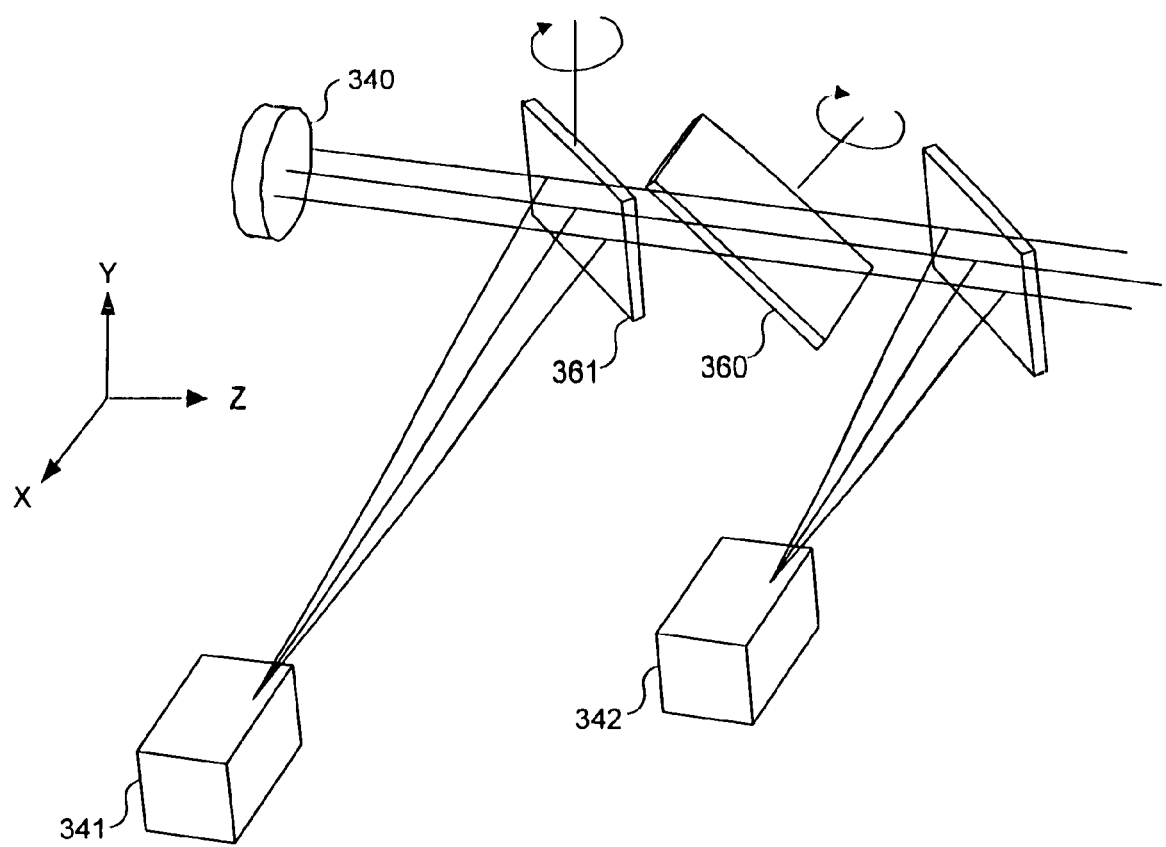
FIG. 27 is an isometric illustration of correction plates that are used to correct for astigmatism induced by a plate beam splitter placed in convergent space.

If plate substrates are employed for dichroic filters 345-347, then astigmatism dominates the aberrations. Astigmatism is imparted in the transmitted wavefront through a plate dichroic filter, but, as shown in FIG. 27, can effectively be cancelled by inserting a clear correction plate 360 of approximately the same thickness, incident angle, and glass type. However, correction plate 360 must be rotated 90 degrees about the Z axis with respect to dichroic filter 361. Correction plate 360, and dichroic filter 361 impart an equal but opposite amount of astigmatism in the transmitted wavefront, so that the astigmatism they contribute cancel. Therefore, light striking detector 342 is free of astigmatism. This configuration leaves a small amount of residual coma. Yet, the optical performance is very close to the diffraction limit. Those of ordinary skill in the art will appreciate that the correction plate can be placed in many alternative positions, with adjustments in its thickness, material, and/or angle, relative to the propagation path of the light. Any of the non-distorting spectral dispersing embodiments can be constructed using an additional objective lens 48 and slit 52, to form a confocal stop arrangement as shown in FIG. 26. FIG. 28 illustrates an embodiment similar to FIG. 25, using multiple imaging lenses; however, the majority of detectors are placed in the transmission path of the dichroic filters. Either of the multiple detector embodiments may be constructed such that the detectors receive light transmitted through the dichroic filters, light reflected by the dichroic filters, or a combination of transmitted and reflected light, as illustrated in both FIGS. 26 and 28.

Wide-Field Decomposition Imaging

Figure 24:
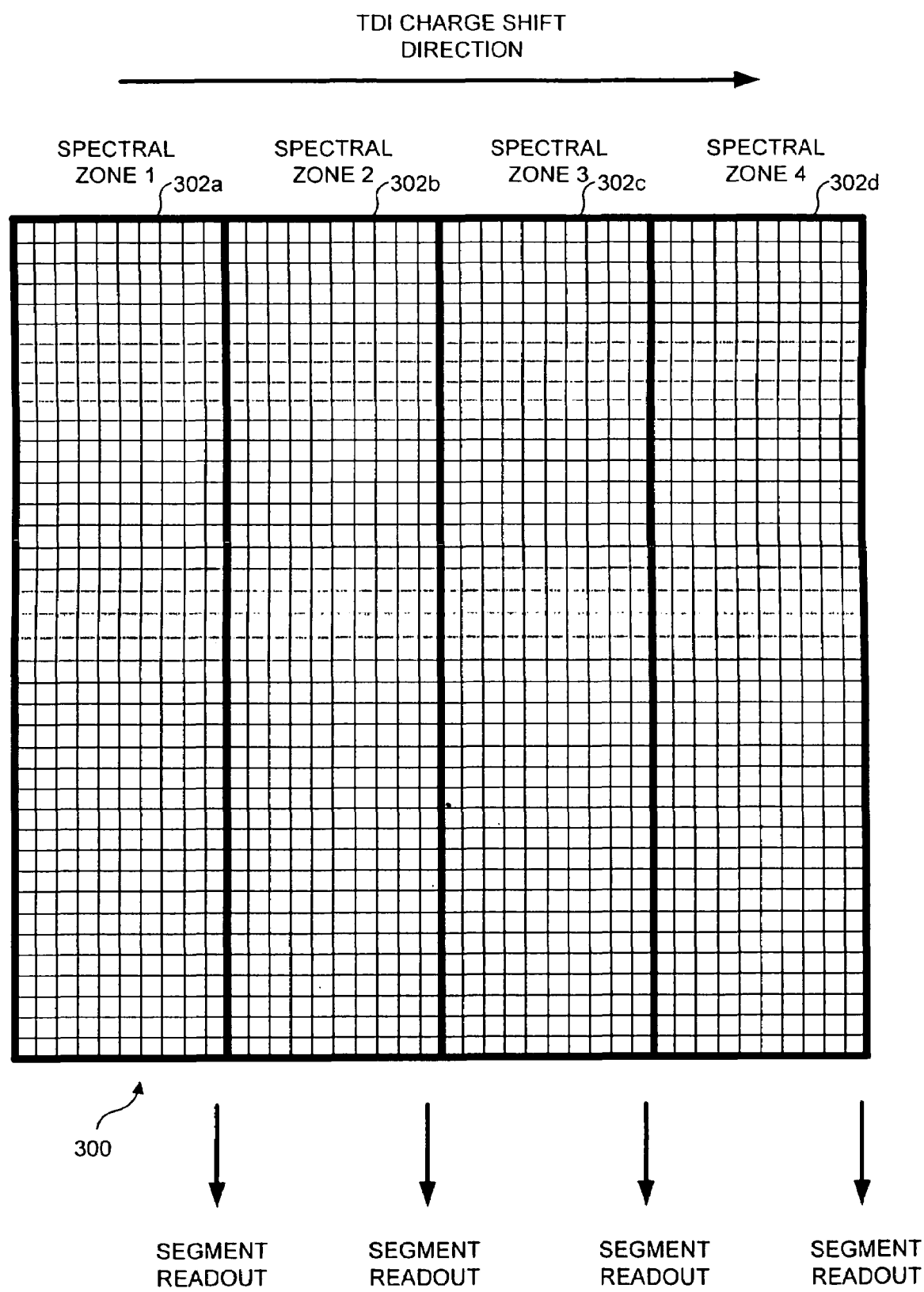
FIG. 24 is a schematic plan view of a spectrally segmented detector for use in detecting and imaging light of several different spectral compositions.

By using a segmented TDI detector 300, as shown in FIG. 24, the present invention can be used to image wide fields of view to increase throughput. In this manner, cells or other objects may be oriented side-by-side such as may be found in broad flat flow, or on microscope slides and microtiter plates. This configuration enables more objects to be imaged simultaneously than could otherwise be possible if objects were aligned in a single file orientation.

Figure 23:
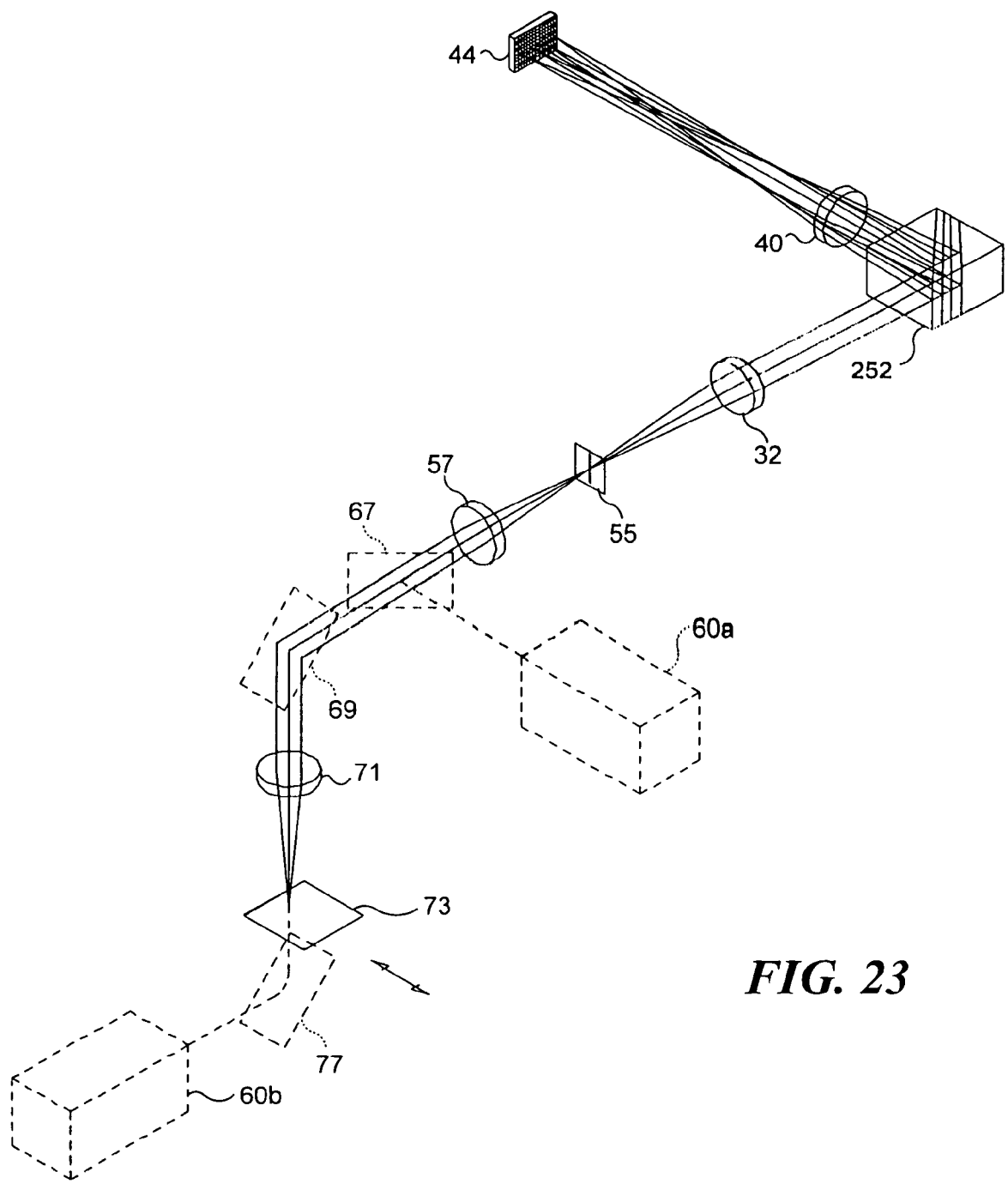
FIG. 23 is a schematic isometric view of yet another embodiment, in which spectral decomposition occurs in an axis that is generally parallel to a direction of motion of a substrate carrying an object.

FIG. 23 illustrates an embodiment of the present invention that facilitates imaging of a wide field. In FIG. 23, motion of a substrate 73 is generally parallel or aligned with an axis of spectral decomposition provided by dichroic element 252. Optional epi illuminator 60a, which may comprise a laser or other type of illumination source, can be used to illuminate objects carried on substrate 73, while there is relative movement between the substrate and the imaging system in the direction of the double-headed arrow. Optionally, another illuminator 60b is provided to provide bright field illumination of the objects on the substrate with light reflected from a reflective surface 77. Light from the objects on substrate 73 passes through a lens 71, is reflected from a reflective surface 69, passes through a dichroic (or partially reflective) mirror 67, and is focused on a slit 55 by a lens 57. Collection lens 32 collimates the light from the slit and directs the light onto dichroic element 252, which spectrally disperses the light passing through lens 40 and onto different regions of detector 44.

Segmented detector 300 (FIG. 24) is used for detector 44 in FIG. 23, and spectral dispersing filter assembly 252 is oriented to decompose light in an axis parallel to the movement of the image across detector 44. As noted above, the field of view of substrate 73 in FIG. 23 may be illuminated in bright field with bright field illuminator 60b or with epi-illumination by illuminator 60a. In either case the illuminated field of view, when imaged by the optical system, is equivalent in size to one segment of detector 300.

As discussed above, when spectral dispersing filter assembly 252 is employed, light is split into a plurality of light beams each having a different bandwidth. Each light beam thus produced is directed at a different nominal angle so as to fall upon a different segment of detector 300. The nominal angular separation between each bandwidth produced by spectral dispersing filter assembly 252 exceeds the field angle of the imaging system in object space, thereby preventing overlap of the field images of various bandwidths on the detector. Therefore, each detector segment sees the same field of view; however, each segment sees light composed of a different spectral bandwidth. Slit 55 may be provided to eliminate any stray light from outside the intended field of view from passing through the system and reaching an inappropriate zone of detector 300.

In the illustrated embodiment, segmented detector 300 comprises four segments or zones 302a-302d, each zone receiving light of a different characteristic. The detector is segmented into these zones such that the charge corresponding to an incident image flows across a segment in concert with the image movement across that segment The charge is then read out of the segment and not permitted to enter an adjacent segment or zone where light of a different characteristic is imaged. Optionally, the charge corresponding to an image received by each zone is integrated over a length of the zone and readout from the tap provided for the zone. In addition, the rate at which the charge is read out from each zone is optionally independently controllable. In summary, this embodiment of the present invention enables a wide field of view to be imaged and decomposed onto the detector such that light of multiple characteristics can be simultaneously collected and analyzed.

Methods to Enhance the Analysis Rate for Imaging Systems including TDI Detectors Currently, the first commercial embodiment to be sold under the ImageStreaM™ product line performs multispectral high resolution imaging of cells or particulates in flow and uses a TDI charge coupled detector (CCD) camera that operates at a line read out rate of 50 kHz. This read out rate, in combination with the system specifications, yields the cell analysis rates shown in Table 1.0. The calculation of these analysis rates is described in Appendix A. As shown in this table, the rate is proportional to the cell or particulate concentration and is equal to 125 objects per second when the object concentration is $5.0 \times 10^7$ objects/ml.

TABLE 1.0

| Cell Concentration (cells/ml) | Cell Detection Rate (0.5 µm pixel resolution and 50 kHz Line Read Out Rate) |
|---|---|
| $10^6$ | 2.5 |
| $10^7$ | 25 |
| $5.0 \times 10^7$ | 125 |

The cell analysis rate that is achieved by the present invention, and the six channels of multimode imagery (brightfield, dark field, and four fluorescent images) offer an unprecedented ability to analyze cells in flow. This system offers an immediate solution for analyzing tens of thousands of cells, is clearly applicable to rare cell detection (i.e., 1 part in 10,000), and is finding immediate application in cell cycle analysis, calcium flux, cell division assessment, cell viability and apoptosis staging, and necrosis differentiation.

The ability to accumulate morphological data rapidly, combined with the powerful quantitative tools being developed, will enable new levels of cell analysis and classification. With the multispectral image data and throughput of the present invention being several orders of magnitude higher than prior art microscopy-based systems, researchers will enjoy highly detailed information about cells. A number of application kits are being developed to replace and enhance microscopy including: chromogenic cell morphological classification, enzymology in flow, phagocytosis, and oxidative bursts.

Additionally, using proprietary fluorescent in situ hybridization (FISH) protocols enables probing specific sequences of DNA and RNA of cells that are in suspension (not limited to histocical slide-based FISH analysis). Adaptation of FISH to cells in suspension (FISHIS), combined with the multispectral imaging data of the system, should be usable in applications that previously required weeks of tedious analysis. For example, the detection of sperm aneuploidy can be performed in hours using FISHIS and the present invention. Additional applications include: the detection of specific gene amplification, detection of gene rearrangement, MRNA expression, and the detection of chromosomal aneuploidy.

The robust data collection and analysis capabilities of the system in accord with the present invention are likely to be employed in other clinical diagnostics areas. Such areas include: diagnostics (oncology), minimal residual disease detection (oncology), cell identification and classification (hematology), aneuploidy assessment in sperm (fertility/reproductive medicine) and non-invasive fetal chromosome assessment (prenatal medicine).

However, even though the current analysis rate is sufficient for many of the previously stated applications, there are number of these applications in which a rare cell detection event is still much more rare. Specifically, the present invention can be used to detect events at the rate of 1 in 1 million, 1 in 10 million, or even greater rarity in the case of non-invasive fetal chromosome assessment and early cancer detection.

Towards this end, the fastest prior art cell analysis instruments on the market today (flow cytometers) have cell analysis rates of up to 20 to 70 thousand cells per second. It is important to note that such instruments represent multiple generation advancements of non-imaging based flow cytometers. Moreover, such instruments yield only multiple univariate parameters, specifically scattered or fluorescent light intensity of up to 14 different channels. In contrast, the present invention readily achieves six different multispectral images, with each cell image composed of approximately 300 pixels. Thus, the present invention provides ultra high content information regarding cells, compared to the faster flow cytometers.

In order to achieve higher cell detection rate for the present invention, there are a number of approaches that are applicable, as follows:

The first method uses a multi-tap TDI CCD camera selected to enable a six-fold increase in the current line rate readout rate. Currently, the present invention utilizes a 600 by 512 pixelated (i.e., TDI) CCD detector. This 600 row element detector includes six separate multispectral imaging channels that are read out utilizing one tap. Thus, by incorporating six separate taps to read off the six separate image channels, it should be possible to increase the speed of the camera by a factor of six. The third column of Table 2.0 (below) illustrates the analysis rate that should be possible for the present invention, assuming the use of a multi-tap CCD camera.

The second method uses a rectangular cross section that has an increased area, to allow for increased broad flat flow, instead of a square cross sectional core. This approach is described in U.S. patent application Ser. No. 09/989,031, entitled "Imaging And Analyzing Parameters of Small Moving Objects Such As Cells in Broad Flat Flow." Utilizing this approach is expected to further increase the analysis rate by a factor of four. The fourth column of Table 2.0 illustrates the analysis rate that should be achieved by the present invention, assuming both the use of a multi-tap CCD camera and broad flat flow.

The third technique uses binning of the vertical CCD elements such that the number of rows decrease, thereby increasing the effective read out rate. Currently the commercial CCD detector used in the preferred embodiment allows for the binning of 1, 2, 4, or 8 vertical pixels, resulting in a vertical image resolution of 0.5, 1.0, 2.0, and 4.0 microns, respectively. This decrease in vertical image resolution provides an increase in analysis rate of up to a factor of eight. It is important to note that this binning is only in the vertical direction and that there is no binning in the horizontal direction.

FIG. 28A illustrates a theoretical black and white image of a ten micron cell over laid on top of a pixilated detector with 0.5 micron resolution in both the horizontal and vertical direction. FIG. 28B illustrates the theoretical image of the ten micron cell imaged with the 0.5×0.5 micron pixilated CCD detector. FIG. 28C illustrates the theoretical image of the cell as a result of the binning together of two vertical pixels when the detector is read out via TDI. FIG. 28D illustrates the theoretical image of the cell when four vertical pixels are binned together. And finally, FIG. 28E illustrates the theoretical image of the cell when the eight vertical pixels are binned together.

Table 2.0 illustrates the potential increases in the analysis rate of the present invention, by employing binning, use of a multi-tap CCD camera, and use of broad field flat flow. In this table, a concentration of $5.0 \times 10^7$ cells/ml is assumed.

TABLE 2.0

| CCD Binning | Configuration | | |
|---|---|---|---|
| | IS 100 | Multi-Tap Camera | Broad Flat Flow |
| 1 pixel—0.5 μm Res | 125 | 750 | 3000 |
| 2 pixels—1.0 μm Res. | 250 | 1500 | 6000 |
| 4 pixels—2.0 μm Res | 500 | 3000 | 12,000 |
| 8 pixels—4.0 μm Res. | 1000 | 6000 | 24,000 |

Based on the cell analysis rates shown in Table 2.0, it is evident that the present invention can be tailored to perform high resolution microscopy in flow at rates as high as 3,000 cells/sec, and, by adjusting the binning of the CCD in software, rates of near 25,000 cells/sec can be achieved, which is similar to the rates of the current highest flow cytometers, while yielding images with a resolution of 0.5×4.0 microns.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

APPENDIX A

Cell Analysis Rates vs. Concentration

The TDI detector of the present invention currently operates at 50 kHz line read out rate, which translates to a velocity of 25 mm/sec in image space, assuming a pixel line height of 0.5 microns.

| | |
|---|---|
| TDI CCD Line Read Out Rate | = 50 kHz |
| TDI Line (Pixel) height in image space | = 0.5 microns |
| Velocity of Synchronized Core Fluid in image space | = 50,000 line/sec * 0.5 μm/sec<br>= 25 mm/sec |
| Core Fluid Volume analyzed per second | = core area * length traveled/sec |
| Assuming a square cross-section of 100 μm² | = 10 μm * 10 μm * 25 mm<br>= $10 \times 10^{-6}$ m * $10 \times 10^{-6}$ m * .025 m<br>= $2.5 \times 10^{-12}$ m³<br>= $2.5 \times 10^{-12}$ m³ * (1 m³/$10^9$ mm³)<br>= $2.5 \times 10^{-3}$ mm³<br>= 2.5 nanoliters |
| Assuming a concentration $10^6$ cells/ml, the number of cells in a 2.5 nanoliter sample that is analyzed every second is: | = $10^6$ cells/ml * 2.5 nl * $10^{-6}$ (ml/nl)<br>= 2.5 cells/sec |

| Cell Concentration | Cells Detection Rate (0.5 mm pixel and 50 kHz) |
|---|---|
| $10^6$ | 2.5 |
| $10^7$ | 25 |
| $5.0 \times 10^7$ | 125 |

The invention in which an exclusive right is claimed is defined by the following:

1. An imaging system configured to produce a plurality of images of an object while there is relative movement between the object and the imaging system, comprising:
    (a) a collection lens disposed so that light traveling from the object passes through the collection lens and travels along a collection path;
    (b) a light dispersing element disposed in the collection path so as to disperse the light that has passed through the collection lens in a plane that is orthogonal to a direction of the relative movement between the object and the imaging system, thereby producing dispersed light;
    (c) an imaging lens disposed to focus the dispersed light, producing focused dispersed light; and
    (d) a detector disposed to receive the focused dispersed light, such that the focused dispersed light incident on the detector comprises a plurality of images of the object.

2. The imaging system of claim 1, wherein the light dispersing element spectrally disperses the light that has passed through the collection lens, and wherein the focused dispersed light is spectrally dispersed across the detector.

3. The imaging system of claim 1, wherein the detector comprises a time delay integration detector.

4. The imaging system of claim 1, further comprising at least one light source configured and disposed such that the plurality of images of the object incident on the detector include at least one fluorescent image and at least one image corresponding to:
    (a) light scattered from the object; and
    (b) light reflected from the object.

5. The imaging system of claim 1, further comprising at least one light source configured and disposed such that the plurality of images of the object incident on the detector include at least one fluorescent image and at least one dark field image.

6. The imaging system of claim 1, further comprising at least one light source configured and disposed such that the plurality of images of the object incident on the detector include at least one fluorescent image, at least one dark field image, and at least one bright field image.

7. The imaging system of claim 1, further comprising at least one light source configured and disposed such that the plurality of images of the object incident on the detector include at least one image corresponding to light emitted from the object, and at least one image corresponding to:
  (a) light scattered from the object; and
  (b) light reflected from the object.

8. The imaging system of claim 1, further comprising at least one light source configured such that the plurality of images of the object incident on the detector include at least one image corresponding to:
  (a) a first type of light from the object, the first type of light comprising light emitted from the object; and
  (b) a second type of light from the object, the second type of light comprising at least one of light scattered by the object and light reflected by the object.

9. The imaging system of claim 8, wherein the first type of light comprises fluorescent light.

10. The imaging system of claim 8, wherein the second type of light comprises at least one of light corresponding to a dark field illumination and light corresponding a bright field illumination.

11. An imaging system configured to produce a plurality of images of an object while there is relative movement between the object and the imaging system, comprising:
  (a) a collection lens disposed so that light traveling from the object passes through the collection lens and travels along a collection path;
  (b) a light dispersing element disposed in the collection path so as to disperse the light that has passed through the collection lens, thereby producing dispersed light;
  (c) an imaging lens disposed to focus the dispersed light, producing focused dispersed light;
  (d) a detector disposed to receive the focused dispersed light, such that the focused dispersed light incident on the detector comprises a plurality of images of the object; and
  (e) at least one light source configured such that the plurality of images of the object incident on the detector include at least one image corresponding to:
    (i) light emitted from the object; and
    (ii) at least one of light scattered by the object and light reflected by the object.

12. The imaging system of claim 11, wherein the light emitted from the object comprises fluorescent light, such that at least one of the plurality of images corresponds to the fluorescent light.

13. The imaging system of claim 11, wherein the detector comprises a time delay integration detector.

14. An imaging system configured to produce a plurality of images of an object while there is relative movement between the object and the imaging system, comprising:
  (a) a collection lens disposed so that light traveling from the object passes through the collection lens and travels along a collection path;
  (b) a light dispersing element disposed in the collection path so as to disperse the light that has passed through the collection lens, thereby producing dispersed light;
  (c) an imaging lens disposed to focus the dispersed light, producing focused dispersed light;
  (d) a detector disposed to receive the focused dispersed light, such that the focused dispersed light incident on the detector comprises a plurality of images of the object; and
  (e) at least one light source configured such that the plurality of images of the object incident on the detector include at least two of the following types of images:
    (i) at least one fluorescent image;
    (ii) at least one dark field image; and
    (iii) at least one bright field image.

15. The imaging system of claim 14, wherein the plurality of images of the object incident on the detector include at least one fluorescent image, at least one dark field image, and at least one bright field image.

16. An imaging system configured to simultaneously produce a plurality of images of an object entrained in a flow of fluid, comprising:
  (a) a fluid channel configured to direct the flow of fluid in which the object is entrained into a field of view;
  (b) a collection lens disposed so that light traveling from the object passes through the collection lens and travels along a collection path;
  (c) a light dispersing element disposed in the collection path so as to disperse the light that has passed through the collection lens, thereby producing dispersed light;
  (d) an imaging lens disposed to focus the dispersed light, producing focused dispersed light; and
  (e) at least one detector disposed to receive the focused dispersed light, such that the focused dispersed light incident on the at least one detector comprises a plurality of images of the object.

17. The imaging system of claim 16, wherein the light dispersing element spectrally disperses the light that has passed through the collection lens, and wherein the focused dispersed light is spectrally dispersed across the at least one detector.

18. The imaging system of claim 16, wherein each at least one detector comprises a time delay integration detector.

19. The imaging system of claim 16, wherein the field of view and the at least one detector are configured to enable more than one object to be imaged simultaneously.

20. The imaging system of claim 16, further comprising at least one light source configured such that the plurality of images of the object incident on the at least one detector include at least one image corresponding to:
  (a) light emitted from the object; and
  (b) at least one of light scattered by the object and light reflected by the object.

21. The imaging system of claim 20, wherein the light emitted from the object comprises fluorescent light, such that at least one of the plurality of images corresponds to the fluorescent light.

22. The imaging system of claim 20, wherein the at least one light source is configured such that the plurality of images of the object incident on the at least one detector include at least one dark field image.

23. The imaging system of claim 20, wherein the at least one light source is configured such that the plurality of images of the object incident on the at least one detector include at least one bright field image.

24. A method for simultaneously producing a plurality of images of an object while there is relative movement between the object and an imaging system, comprising the steps of:

(a) focusing light from the object along a collection path that is in a different direction than the relative movement between the object and the imaging system;
(b) dispersing the light that is traveling along the collection path, producing dispersed light in a plane that is orthogonal to a direction of the relative movement between the object and the imaging system;
(c) focusing the dispersed light to produce a plurality of dispersed images; and
(d) providing at least one detector disposed to receive the plurality of dispersed images.

25. The method of claim 24, further comprising the step of determining at least one characteristic of the object, by comparing the plurality of dispersed images received by the at least one detector.

26. The method of claim 24, further comprising the step of stimulating the object to induce the object to emit light, such that the step of focusing light from the object along a collection path comprises the steps of:
(a) focusing light emitted from the object along the collection path, such that at least one of the plurality of dispersed images corresponds to the light emitted from the object; and
(b) focusing at least one of light scattered by the object and light reflected by the object along the collection path, such that at least one of the plurality of dispersed images corresponds to at least one of light scattered by the object and light reflected by the object.

27. The method of claim 24, wherein the step of focusing light from the object along a collection path comprises the steps of:
(a) focusing light emitted from the object along the collection path, such that at least one of the plurality of dispersed images corresponds to the light emitted from the object; and
(b) focusing at least one of light scattered by the object and light reflected by the object along the collection path, such that at least one of the plurality of dispersed images corresponds to at least one of light scattered by the object and light reflected by the object.

28. The method of claim 27, further comprising the step of directing light toward the object to achieve a dark field illumination, such that at least one of the plurality of dispersed images corresponds to a dark field image.

29. The method of claim 27, further comprising the step of directing light toward the object to achieve a bright field illumination, such that at least one of the plurality of dispersed images corresponds to a bright field image.

30. The method of claim 24, wherein the step of providing at least one detector further comprises the step of providing a time delay integration detector.

31. A method for simultaneously producing a plurality of images of an object while there is relative movement between the object and an imaging system, wherein at least one of the plurality of images corresponds to light emitted from the object, and at least one the plurality of images corresponds to at least one of light scattered by the object and light reflected by the object, comprising the steps of:
(a) focusing light from the object along a collection path, such light from the object including light emitted by the object, and at least one of:
  (i) light to be used to generate at least one dark field image; and
  (ii) light to be used to generate at least one bright field image; and
(b) dispersing the light from the object that is traveling along the collection path, producing dispersed light;
(c) focusing the dispersed light to produce a plurality of images; and
(d) providing at least one detector disposed to receive the plurality of images, the plurality of images including at least one image corresponding to light emitted by the object, and at least one of the following types of images:
  (i) dark field images; and
  (ii) bright field images.

32. The method of claim 31, further comprising the step of determining at least one characteristic of the object, by comparing the plurality of images received by the detector.

33. The method of claim 31, further comprising the step of stimulating the object to induce the object to emit light.

34. The method of claim 31, further comprising the step of directing light toward the object to achieve a dark field illumination, such that at least one of the plurality of images received by the detector corresponds to a dark field image.

35. The method of claim 31, further comprising the step of directing light toward the object to achieve a bright field illumination, such that at least one of the plurality of images received by the detector corresponds to a bright field image.

36. The method of claim 31, wherein the step of providing at least one detector further comprises the step of providing a time delay integration detector.

37. A method for simultaneously producing a plurality of images of an object entrained in a flow of fluid, comprising the steps of:
(a) introducing the object entrained in the flow of fluid into a fluid channel;
(b) directing light from the object along a collection path;
(c) dispersing the light from the object that is traveling along the collection path, producing dispersed light;
(d) focusing the dispersed light to produce a plurality of images; and
(e) providing at least one detector disposed to receive the plurality of images.

38. The method of claim 37, further comprising the step of determining at least one characteristic of the object, by analyzing the plurality of images received by the detector.

39. The method of claim 37, further comprising the step of stimulating the object to induce the object to emit light, such that the step of focusing light from the object along a collection path comprises the steps of:
(a) focusing light emitted from the object along the collection path, such that at least one of the plurality of images corresponds to the light emitted from the object; and
(b) focusing at least one of light scattered by the object and light reflected by the object along the collection path, such that at least one of the plurality of images corresponds to at least one of light scattered by the object and light reflected by the object.

40. The method of claim 37, wherein the step of focusing light from the object along a collection path comprises the steps of:
(a) focusing light emitted from the object along the collection path, such that at least one of the plurality of images corresponds to the light emitted from the object; and
(b) focusing at least one of light scattered by the object and light reflected by the object along the collection path, such that at least one of the plurality of images corresponds to at least one of light scattered by the object and light reflected by the object.

41. The method of claim 40, further comprising the step of directing light toward the object to achieve a dark field illumination, such that at least one of the plurality of images corresponds to a dark field image.

42. The method of claim 40, further comprising the step of directing light toward the object to achieve a bright field illumination, such that at least one of the plurality of images corresponds to a bright field image.

43. The method of claim 37, wherein the step of dispersing the light that is traveling along the collection path comprises the step of producing dispersed light in a plane that is orthogonal to a direction of the flow of fluid.

44. The method of claim 37, wherein the step of providing at least one detector further comprises the step of providing a time delay integration detector.

45. A method for determining one or more characteristics of an object using multi spectral imaging, while there is relative movement between the object and an imaging system used to obtain a plurality of spectral images, comprising the steps of:
- (a) providing an object including at least one element that can be spectrally distinguished based on at least one of:
  - (i) light scattered by such an element;
  - (ii) light reflected by such an element; and
  - (iii) light emitted by such an element;
- (b) focusing light from the object along a collection path;
- (c) dispersing the light that is traveling along the collection path, producing spectrally dispersed light;
- (d) focusing the spectrally dispersed light to produce the plurality of spectral images corresponding to the object;
- (e) providing at least one detector disposed to receive the plurality of spectral images; and
- (f) analyzing the plurality of spectral images received by the at least one detector to determine at least one characteristic of the object.

46. The method of claim 45, further comprising the step of directing light toward the object to achieve a dark field illumination, such that at least one of the plurality of spectral images corresponds to a dark field image.

47. The method of claim 45, further comprising the step of directing light toward the object to achieve a bright field illumination, such that at least one of the plurality of spectral images corresponds to a bright field image.

48. The method of claim 45, wherein the object is a biological cell.

49. The method of claim 45, further comprising the step of directing light toward the object to stimulate an emission from at least one element, such that at least one of the plurality of images corresponds to light emitted by that element.

50. The method of claim 45, wherein the step of dispersing the light that is traveling along the collection path comprises the step of producing dispersed light in a plane that is orthogonal to a direction of the relative movement between the object and the imaging system.

51. The method of claim 45, wherein the object is entrained in a flow of fluid, and further comprising the step of introducing the object entrained in the flow of fluid into a fluid channel that includes a field of view associated with the imaging system.

52. The method of claim 45, wherein the step of focusing light from the object along a collection path comprises the steps of:
- (a) focusing light emitted from the object along the collection path, such that at least one of the plurality of images corresponds to the light emitted from the object; and
- (b) focusing at least one of light scattered by the object and light reflected by the object along the collection path, such that at least one of the plurality of images corresponds to at least one of light scattered by the object and light reflected by the object.

53. The method of claim 45, wherein the step of providing at least one detector further comprises the step of providing a time delay integration detector.

* * * * *